(12) United States Patent
Parkar et al.

(10) Patent No.: US 11,602,412 B2
(45) Date of Patent: Mar. 14, 2023

(54) PRINTABLE COMPOSITIONS INCLUDING POLYMERIC AND POLYMERIZABLE COMPONENTS, ARTICLES, AND METHODS OF MAKING ARTICLES THEREFROM

(71) Applicant: 3M INNOVATIVE PROPERTIES COMPANY, St. Paul, MN (US)

(72) Inventors: Zeba Parkar, Marietta, GA (US); Alexander J. Huffman, St. Paul, MN (US); Mahfuza B. Ali, Mendota Heights, MN (US); Stephen A. Johnson, Woodbury, MN (US); Victor Ho, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 276 days.

(21) Appl. No.: 16/463,560

(22) PCT Filed: Dec. 20, 2017

(86) PCT No.: PCT/US2017/067498
§ 371 (c)(1),
(2) Date: May 23, 2019

(87) PCT Pub. No.: WO2018/119026
PCT Pub. Date: Jun. 28, 2018

(65) Prior Publication Data
US 2019/0374309 A1 Dec. 12, 2019

Related U.S. Application Data

(60) Provisional application No. 62/477,038, filed on Mar. 27, 2017, provisional application No. 62/438,613, filed on Dec. 23, 2016.

(51) Int. Cl.
*A61C 7/08* (2006.01)
*B33Y 10/00* (2015.01)
(Continued)

(52) U.S. Cl.
CPC ............. *A61C 7/08* (2013.01); *A61K 6/887* (2020.01); *A61K 6/893* (2020.01); *B29C 64/124* (2017.08);
(Continued)

(58) Field of Classification Search
None
See application file for complete search history.

(56) References Cited

U.S. PATENT DOCUMENTS

| 2,858,295 A | 10/1958 | Melamed |
| 3,429,722 A | 2/1969 | Economy |

(Continued)

FOREIGN PATENT DOCUMENTS

| CN | 1933961 A | 3/2007 |
| CN | 101776844 A | 7/2010 |

(Continued)

OTHER PUBLICATIONS

International Search report for PCT International Application No. PCT/US2017/067498 dated May 24, 2018, 7 pages.

*Primary Examiner* — Robert J Grun
(74) *Attorney, Agent, or Firm* — Adrian L. Pishko

(57) ABSTRACT

The present disclosure provides a printable composition. The printable composition includes a polymer, a polymerizable component, a temporary solvent, a photoinitiator, and optionally an inhibitor. The present disclosure also provides an article including an integral blend of a thermoset polymer and a second polymer different from the thermoset polymer. Further, the present disclosure provides a method of making an article. The method includes (i) providing a printable composition; (ii) selectively curing the printable composition to form a gelled article; and (iii) removing at least a portion of the temporary solvent from the gelled article. The method may optionally include (iv) curing unpolymerized
(Continued)

polymerizable component remaining before or after step (iii). Also, methods are provided, including receiving, by a manufacturing device having one or more processors, a digital object comprising data specifying a plurality of layers of an article, the article including: an integral blend of 8 to 50 wt. %, inclusive, of a thermoset polymer and 30 to 90 wt. %, inclusive, of a second polymer different from the thermoset polymer, wherein the weight percent is based on the total weight of the article; and generating, with the manufacturing device by an additive manufacturing process, the article based on the digital object. A system is provided, including a display that displays a 3D model of an article; and one or more processors that, in response to the 3D model selected by a user, cause a 3D printer to create a physical object of an article.

7 Claims, 6 Drawing Sheets

(51) Int. Cl.
| | |
|---|---|
| B33Y 30/00 | (2015.01) |
| B33Y 50/02 | (2015.01) |
| B33Y 70/00 | (2020.01) |
| B29C 64/124 | (2017.01) |
| B29C 64/20 | (2017.01) |
| B29C 64/393 | (2017.01) |
| C08F 220/68 | (2006.01) |
| C08L 75/04 | (2006.01) |
| A61K 6/887 | (2020.01) |
| A61K 6/893 | (2020.01) |
| B33Y 70/10 | (2020.01) |
| B29K 101/12 | (2006.01) |
| B29L 31/00 | (2006.01) |

(52) U.S. Cl.
CPC ............ *B29C 64/20* (2017.08); *B29C 64/393* (2017.08); *B33Y 10/00* (2014.12); *B33Y 30/00* (2014.12); *B33Y 50/02* (2014.12); *B33Y 70/10* (2020.01); *C08F 220/68* (2013.01); *C08L 75/04* (2013.01); *B29K 2101/12* (2013.01); *B29L 2031/7532* (2013.01); *C08L 2201/56* (2013.01)

(56) References Cited

U.S. PATENT DOCUMENTS

| | | | |
|---|---|---|---|
| 3,479,310 A | 11/1969 | Dieterich | |
| 3,795,524 A | 3/1974 | Sowman | |
| 4,047,965 A | 9/1977 | Karst | |
| 4,307,219 A | 12/1981 | Larson | |
| 4,480,085 A | 10/1984 | Larson | |
| 4,543,315 A | 9/1985 | Lorenz | |
| 4,642,126 A | 2/1987 | Zador | |
| 4,652,274 A | 3/1987 | Boettcher | |
| 4,954,462 A | 9/1990 | Wood | |
| 5,185,299 A | 2/1993 | Wood | |
| 5,427,835 A | 6/1995 | Morrison | |
| 5,772,947 A | 6/1998 | Hull | |
| 5,780,154 A | 7/1998 | Okano | |
| 5,981,621 A | 11/1999 | Clark | |
| 6,183,593 B1 | 2/2001 | Narang | |
| 6,200,732 B1 * | 3/2001 | Tamura | ............... G03F 7/0037 430/284.1 |
| 6,368,769 B1 | 4/2002 | Ohkawa | |
| 6,811,937 B2 | 11/2004 | Lawton | |
| 8,097,399 B2 | 1/2012 | Patel | |
| 8,329,776 B2 | 12/2012 | Hecht | |
| 8,778,235 B2 | 7/2014 | Ito | |
| 8,980,971 B2 | 3/2015 | Ueda | |
| 9,295,617 B2 | 3/2016 | Eckert | |
| 2001/0003031 A1 | 6/2001 | Tamura | |
| 2002/0149137 A1 | 10/2002 | Jang | |
| 2007/0031791 A1 | 2/2007 | Cinader | |
| 2008/0171156 A1 | 7/2008 | Olijve et al. | |
| 2008/0182914 A1 | 7/2008 | Itami et al. | |
| 2008/0248442 A1 | 10/2008 | Raby | |
| 2009/0045752 A1 | 2/2009 | Azuma | |
| 2011/0091832 A1 | 4/2011 | Kim | |
| 2013/0095446 A1 | 4/2013 | Andreiko | |
| 2014/0239527 A1 | 8/2014 | Lee | |
| 2014/0356799 A1 | 12/2014 | Cinader, Jr | |
| 2015/0044623 A1 | 2/2015 | Rundlett | |
| 2016/0137839 A1 | 5/2016 | Rolland | |
| 2016/0256240 A1 | 9/2016 | Shivapuja | |

FOREIGN PATENT DOCUMENTS

| | | | |
|---|---|---|---|
| CN | 104085107 A | 10/2014 | |
| CN | 105259736 A | 1/2016 | |
| EP | 2008636 | 12/2008 | |
| EP | 2011075671 | 4/2011 | |
| JP | H09194540 | 7/1997 | |
| JP | 2009-502583 A | 1/2009 | |
| JP | 2009-503225 A | 1/2009 | |
| JP | 2013-101185 | 5/2013 | |
| WO | WO-03044103 A1 * | 5/2003 | ............ C09D 11/30 |
| WO | WO 2007-113107 | 10/2007 | |
| WO | WO 2008-125074 | 10/2008 | |
| WO | WO 2009-042378 | 4/2009 | |
| WO | WO 2009-158231 | 12/2009 | |
| WO | WO 2015-094842 | 6/2015 | |
| WO | WO 2015-123170 | 8/2015 | |
| WO | WO 2016-071811 | 5/2016 | |
| WO | WO 2016-109654 | 7/2016 | |
| WO | WO 2016-109660 | 7/2016 | |
| WO | WO 2016-148960 | 9/2016 | |
| WO | WO 2016-148961 | 9/2016 | |
| WO | WO 2016-149007 | 9/2016 | |
| WO | WO 2016-153711 | 9/2016 | |
| WO | WO 2017-127561 | 7/2017 | |
| WO | WO 2017-197220 | 11/2017 | |
| WO | WO 2018-005501 | 1/2018 | |
| WO | WO 2019-023009 | 1/2019 | |

* cited by examiner

PRINTABLE COMPOSITIONS INCLUDING POLYMERIC AND POLYMERIZABLE COMPONENTS, ARTICLES, AND METHODS OF MAKING ARTICLES THEREFROM

CROSS REFERENCE TO RELATED APPLICATIONS

This application is a national stage filing under 35 U.S.C. 371 of PCT/US2017/067498, filed Dec. 20, 2017, which claims the benefit of U.S. Application No. 62/438,613, filed Dec. 23, 2016 and U.S. Application No. 62/477,,038, filed March 27, 2017, the disclosures of which are incorporated by reference in their entirety herein.

TECHNICAL FIELD

The present disclosure broadly relates to articles including both polymeric and polymerizable components, and methods of making the articles such as additive manufacturing methods.

BACKGROUND

The use of stereolithography and inkjet printing to produce three-dimensional articles has been known for a relatively long time, and these processes are generally known as methods of so called 3D printing (or additive manufacturing). In stereolithography techniques the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is, in general, not yet fully cured and must, normally, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

One particularly attractive opportunity for 3D printing is in the direct creation of orthodontic clear tray aligners. These trays, also known as aligners and polymeric or shell appliances, are provided in a series and are intended to be worn in succession in order to gradually move the teeth in incremental steps toward a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

SUMMARY

Existing printable resins tend to be too brittle (e.g., low elongation, short-chain crosslinked bonds, thermoset composition, and/or high glass transition temperature) for a resilient oral appliance such as an aligner. An aligner or other appliance printed from such resins could easily break in the patient's mouth during treatment, creating material fragments that may abrade or puncture exposed tissue or be swallowed. These fractures at the very least interrupt treatment and could have serious health consequences for the patient. While the brittle nature of the existing resins might be rectified by using polymerizable components in the printable resin with less crosslinking and higher elongation (e.g., hydroxyethyl methacrylate), such resins are prone to lose strength when immersed in water; a problem exacerbated by a moisture rich environment such as a human mouth. Thus, there is a need for curable liquid resin compositions that are tailored and well suited for creation of resilient articles using a 3D printing (e.g., additive manufacturing) method. Preferably, curable liquid resin compositions to be used in the 3D printing process have low viscosity, a proper curing rate, and excellent mechanical properties in both the gelled article (e.g., green body) and the final cured article.

In a first aspect, the present disclosure provides a printable composition. The printable composition includes (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition.

In a second aspect, the present disclosure provides an article. The article includes an integral blend of 8 to 50 wt. %, inclusive, of a thermoset polymer and 30 to 90 wt. %, inclusive, of a second polymer different from the thermoset polymer, where the weight percent is based on the total weight of the article.

In a third aspect, the present disclosure provides a method of making an article. The method includes: (i) providing a printable composition; (ii) selectively curing the printable composition to form a gelled article; and (iii) removing at least a portion of the temporary solvent from the gelled article. The method further includes (iv) optionally curing unpolymerized polymerizable component remaining before or after step (iii). The printable composition includes: (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition.

In a fourth aspect, the present disclosure provides a non-transitory machine readable medium. The non-transitory machine readable medium has data representing a three-dimensional model of an article, when accessed by one or more processors interfacing with a 3D printer, causes the 3D printer to create an article. The article includes an integral blend of 8 to 50 wt. %, inclusive, of a thermoset polymer and 30 to 90 wt. %, inclusive, of a second polymer different from the thermoset polymer. The weight percent is based on the total weight of the article.

In a fifth aspect, the present disclosure provides a method. The method includes retrieving, from a non-transitory machine readable medium, data representing a 3D model of an article. The article includes: an integral blend of 8 to 50 wt. %, inclusive, of a thermoset polymer and 30 to 90 wt. %, inclusive, of a second polymer different from the thermoset polymer. The weight percent is based on the total weight of the article. The method further includes executing, by one or more processors, a 3D printing application interfacing with a manufacturing device using the data; and generating, by the manufacturing device, a physical object of the article.

In a sixth aspect, the present disclosure provides a method. The method includes receiving, by a manufacturing device having one or more processors, a digital object including data specifying a plurality of layers of an article. The article includes an integral blend of 8 to 50 wt. %, inclusive, of a thermoset polymer and 30 to 90 wt. %, inclusive, of a second polymer different from the thermoset polymer. The weight percent is based on the total weight of the article. The method further includes generating, with the manufacturing device by an additive manufacturing process, the article based on the digital object.

In a seventh aspect, the present disclosure provides a system. The system includes a display that displays a 3D model of an article; and one or more processors that, in response to the 3D model selected by a user, cause a 3D printer to create a physical object of an article. The article includes: an integral blend of 8 to 50 wt. %, inclusive, of a thermoset polymer and 30 to 90 wt. %, inclusive, of a second polymer different from the thermoset polymer, wherein the weight percent is based on the total weight of the article.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
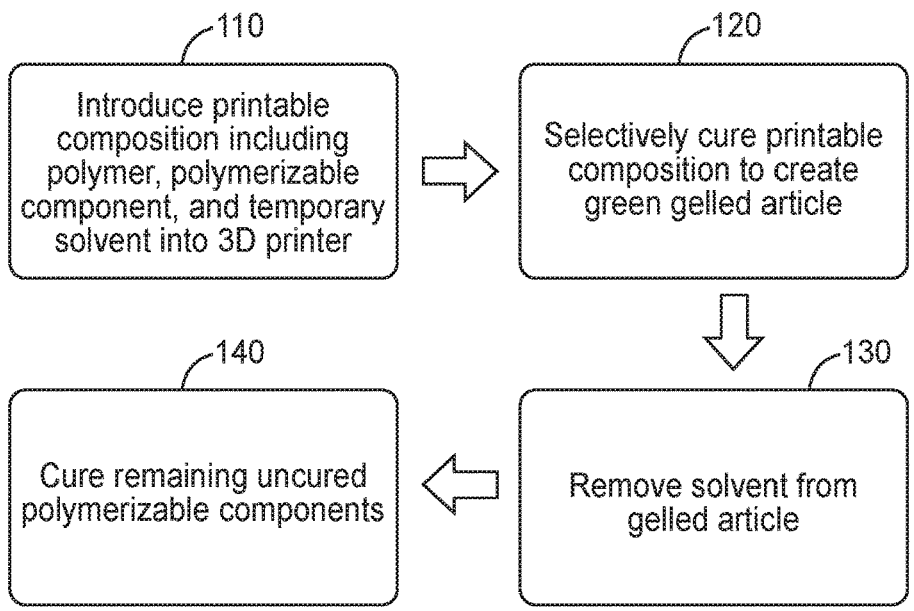
FIG. 1 is a flowchart of a process for building an article using the printable compositions disclosed herein

While the above-identified figures set forth several embodiments of the disclosure other embodiments are also contemplated, as noted in the description. The figures are not necessary drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, the terms "hardenable" refers to a material that can be cured or solidified, e.g., by heating to remove solvent, heating to cause polymerization, chemical crosslinking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

As used herein, "non-crosslinkable" refers to a polymer that does not undergo crosslinking when exposed to actinic radiation or elevated heat. Typically, non-crosslinkable polymers are non-functionalized polymers such that they lack functional groups that would participate in crosslinking.

As used herein, "printable" means that a hardenable composition, prior to polymerization (i.e., hardening), has a viscosity profile consistent with the requirements and parameters of one or more 3D printing systems. Printable compositions according to the present disclosure are photopolymerizable.

As used herein, a "resin" contains all polymerizable components (monomers, oligomers and/or polymers) being present in a hardenable, printable composition. The resin may contain only one polymerizable component compound or a mixture of different polymerizable compounds.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically crosslinked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, the present disclosure provides a printable composition. The printable composition comprises:
(a) 1 to 50 wt. %, inclusive, of a polymer;
(b) 5 to 50 wt. %, inclusive, of a polymerizable component;
(c) 10 to 80 wt. %, inclusive, of a temporary solvent;
(d) 0.1 to 5 wt. %, inclusive, of a photoinitiator; and
(e) an optional inhibitor in an amount of 0.001 to 1 wt. %, inclusive, if present; based on the total weight (i.e., 100 wt. %) of the printable composition. The components (a) through (e) are discussed in detail below.

Polymer

The printable compositions of the present disclosure include at least one polymer. The at least one polymer provides flexibility to the final article (e.g., at least a minimum elongation at break). In some embodiments, the polymer comprises a non-crosslinkable polymer. Inclusion of a non-crosslinkable polymer can be advantageous because when the printable composition is exposed to actinic radiation to polymerize the polymerizable component, the polymer does not crosslink and decrease its elongation capability. Alternatively, in some embodiments the polymer comprises one or more functional groups selected from hydroxyl groups, carboxyl groups, amino groups, and siloxane groups. These functional groups can be reactive with other components of the printable composition during printing, such as the polymerizable composition. Inclusion of a polymer having at least one functional group can be advantageous because it can be desirable to attach the polymer to the polymerizable component to assist in maintaining their interpenetration following printing. In some embodiments, the polymer comprises a thermoplastic polymer. Inclusion of a thermoplastic polymer can be advantageous because the polymer is able to soften or melt with heat and be formed into different shapes without damaging the polymer chains.

Typically, the polymer comprises a weight average molecular weight of 20,000 grams per mole or greater (g/mol), 30,000 g/mol or greater, 40,000 g/mol or greater, 50,000 g/mol or greater, 60,000 g/mol or greater, 70,000 g/mol or greater, 80,000 g/mol or greater, 90,000 g/mol or greater, or 100,000 grams per mole or greater; and 2,000,000 g/mol or less, 1,750,000 g/mol or less, 1,500,000 g/mol or less, 1,250,000 g/mol or less, 1,000,000 g/mol or less, 750,000 g/mol or less, or 500,000 g/mol or less. The weight average molecular weight may be measured by gel permeation chromatography (GPC). The use of polymers having a weight average molecular weight of 20,000 g/mol or greater tend to provide a final article having at least a certain desirable minimum elongation at break.

Suitable polymers include for instance and without limitation, polyethylene (PE), poly(meth)acrylate, polypropylene, polyurethane, sulfopolyester, polycarbonate, polyethylene terephthalate (PET), a thermoplastic fluoropolymer, and combinations thereof. In select embodiments, the polymer comprises poly(meth)acrylate (e.g., poly(methylmethacrylate) (PMMA)).

More particularly, suitable polymers include polyolefins (e.g., polyethylene (such as low density polyethylene (LDPE), medium density polyethylene (MDPE), high density polyethylene (HDPE), and ultra high molecular weight polyethylene (UHMWPE)), polypropylene, polybutylene, ethylene copolymers (e.g., polyethylene terephthalate (PET)), propylene copolymers, butylene copolymers, and copolymers and blends of these polymers). When polypropylene is used, the polypropylene may include alpha and/or beta phase polypropylene. PET includes carboxylate subunits formed from terephthalic acid or esters thereof and glycol subunits formed using ethylene glycol. Polycarbonate is a generic term used to describe polyester polymers containing carbonate groups, and may be produced by the reaction of phosgene with bisphenol A.

Polyurethane is a generic term used to describe polymers prepared by the reaction of a polyfunctional isocyanate with a polyfunctional alcohol to form urethane linkages. The term "polyurethane" has also been used more generically to refer to the reaction products of polyisocyanates with any polyactive hydrogen compound including polyfunctional alcohols, amines, and mercaptans. Polyurethane polymers can be dispersed in water by incorporating stabilizing groups into their backbone. Anionic, cationic, and non-ionic dispersion stabilizing groups have been used. Various aqueous polyurethane dispersions have been prepared by those skilled in the art (e.g., U.S. Pat. No. 3,479,310 (Dieterich et al.) and U.S. Pat. No. 4,307,219 (Larson)). Examples of commercially available polyurethane emulsions include those aqueous aliphatic polyurethane emulsions available as NeoRez R-620, NeoRez R-961 and NeoRez R-966 from DSM. Suitable commercially available polymeric dispersions include for example, an aliphatic polycarbonate/polyurethane dispersion, an aqueous anionic dispersion of an aliphatic polycarbonate polyurethane, a UV-curable polyurethane/acrylic copolymer dispersion, and a UV-curable polyurethane dispersion, each of which is available from Alberdingk Boley (Greensboro, N.C.).

Suitable fluoropolymers include a thermoplastic fluoropolymer obtained by polymerizing one or more types of fluorinated or partially fluorinated monomers. In this case, the specific microstructure of the fluoropolymer allows for a certain degree of crystallinity of the fluoropolymer, giving the thermoplastic properties. Generally, the thermoplastic fluoropolymer is at least a copolymer, but may be a terpolymer or a thermoplastic fluoropolymer that contains even four or more different copolymerizable monomers. Copolymerization allows for the decrease in crystallinity compared to the fluorine-based homopolymer, which can be advantageously used in the pressure-sensitive adhesive composition of this disclosure. Crosslinking of the thermoplastic fluoropolymer can be performed generally with a peroxide, a polyol or a polyamine, but is not limited thereto. The fluoropolymer may be a mixture of chemically different thermoplastic fluoropolymers, as well as, mixtures of chemically different fluoroelastomers and mixtures of thermoplastic fluoropolymers and fluoroelastomers.

For instance, suitable thermoplastic fluoropolymers include copolymers of tetrafluoroethene (TFE) with perfluorinated, partially fluorinated or non-fluorinated comonomers, wherein the comonomer content is 1 wt. % of greater, 3 wt. % or greater, and may be up to 30 wt. % (as used hereinabove and below the weight percentages are based on total weight of the polymer—unless specified otherwise). Examples include: fluorinated ethylene propylene (FEP) (e.g., copolymers of TFE, hexafluoropropylene (HFP), and other optional amounts of perfluorinated vinyl ethers); THV (e.g., copolymers of TFE, vinylidine fluoride (VDF) and HFP), perfluoro alkoxy (PFA) (e.g., copolymers of TFE and perfluoro alkyl vinyl ethers and/or perfluoro alkyl allyl ethers); homonomers and copolymers of VDF (e.g., PVDF); and homo- and copolymers of chlortrifluoroethylene (CTFE) and copolymers of TFE and ethylene (e.g., ETFE). Thermoplastic fluoropolymers (sometimes referred to as fluorothermoplasts or fluorothermoplastics) are described, for example, in "Fluoropolymer, Organic" in Ullmann's Encyclopedia of industrial chemisty, 7th edition, 2013, Wiley-VCH Verlag Chemie, Weinheim, Germany. Preferred fluorothermoplastics include fluoropolymers with a melting point between 260 and 315° C., preferably 280° C. to 315° C.

As used herein, the term "polyester" refers to polyesters made from a single dicarboxylate monomer and a single diol monomer and also to copolyesters which are made from more than one dicarboxylate monomer and/or more than one diol monomer. In general, polyesters are prepared by condensation of the carboxylate groups of the dicarboxylate monomer with hydroxyl groups of the diol monomer. As used herein, the terms "dicarboxylate" and "dicarboxylic acid" are used interchangeably and include lower alkyl esters having from 1 to 10 carbon atoms. As used herein, diol monomers include those monomers having two or more hydroxyl groups, for example, diols, triols, tetraols, and pentaols. In general, useful sulfonated polyesters include those that are water soluble and those that are water dispersible. Molecular weights of from about 8000 to about 50000 may be useful. Amorphous sulfopolyesters described in U.S. Pat. No. 4,480,085 (Larson) may be useful. Sulfopolyesters described in U.S. Pat. No. 5,427,835 (Morrison et al.) may also be useful.

The sulfopolyester comprises at least one dicarboxylate monomer having one or more pendant sulfonate groups. Pendant sulfonate groups are groups that do not participate in polymerization reactions that form the main backbone of polyesters. Examples of sulfonated dicarboxylate monomers include sulfonated derivatives of naphthalenedicarboxylic acid; terephthalic acid; phthalic acid; isophthalic acid; maleic acid; itaconic acid; azelaic acid; adipic acid; sebacic acid; succinic acid; glutamic acid; norbornenedicarboxylic acid; bicyclooctanedicarboxylic acid; 1,6-cyclohexanedicarboxylic acid; t-butylisophthalic acid; tri-mellitic acid; 4,4'-biphenyldicarboxylic acid; anthracenedicarboxylic acid; and tetradecanedicarboxylic acid. Any of the sulfonated dicarboxylate monomers can be substituted by groups having a molecular weight of less than about 80 and which are inert in the polymerization reaction. Examples of inert pendent groups include halogens, cyano, nitro, lower alkyl and alkoxy groups having from 1 to 4 carbon atoms, and phenyl groups. Additional dicarboxylate monomers are described in Larson. The pendant sulfonate groups may be introduced by grafting them onto side chains of a polyester, capping as end groups of a polyester, or including monomers having pendant sulfonated groups during polymerization to form the polyester. Useful sulfopolyesters typically comprise at least two dicarboxylate monomers: one that is sulfonated as described above and one that is not. Unsulfonated dicarboxylate monomers that can be used include any of those described above for sulfonated derivatives.

Suitable poly(meth)acrylate polymers preferably include zwitterionic copolymers or cationic copolymers. The zwitterionic copolymers include the polymerized product of an anionic monomer that is acrylic acid, methacrylic acid, a salt thereof, or a blend thereof; an acrylate or methacrylate ester of an alcohol having between 8 and 12 carbons; and a cationic monomer that is an acrylate or methacrylate ester having alkylammonium functionality. Optionally, one or more additional monomers are included in the zwitterionic copolymers. In some embodiments the anionic monomer is acrylic or methacrylic acid, the acid is converted either before or after polymerization to a corresponding carboxylate salt by neutralization. The cationic copolymers include the polymerized product of polymerizable monomers including at least an acrylate or methacrylate ester of an alcohol having between 8 and 12 carbons and a cationic monomer that is an acrylate or methacrylate ester having an alkylammonium functionality. Optionally, one or more additional monomers are included in the cationic polymers of the invention. In some embodiments, the acrylate or methacrylate ester is a mixture of two or more such esters; in some embodiments, the cationic monomer is a mixture of two or more such cationic monomers.

The acrylate or methacrylate ester of an alcohol having between 8 and 12 carbons may include acrylate or methacrylate esters of linear, branched, or cyclic alcohols (e.g., octyl, isooctyl, nonyl, isononyl, decyl, undecyl, and dodecyl alcohol). The polymerized product of the acrylate or methacrylate ester of an alcohol having between 8 and 12 carbons is present in the cationic polymer at about 50 wt % to 95 wt % of the total weight of the polymer, or at about 60 wt % to 90 wt % of the total weight of the polymer, or at about 75 wt % to 85 wt % of the total weight of the polymer.

Often, the cationic monomer is an acrylate or methacrylate ester including an alkylammonium functionality, such as a 2-(trialkyl ammonium)ethyl acrylate or a 2-(trialkylammonium)ethyl methacrylate. A suitable monomer includes for example dimethylaminoethyl acrylate methyl chloride quaternary, available under the trade designation AGEFLEX FA1Q80MC from BASF (Ludwigshafen, Germany). The anion associated with the ammonium functionality of the cationic monomer is not particularly limited. In some embodiments, the anion is a halide anion (such as chloride, bromide, fluoride, or iodide), $BF_4$, $N(SO_2CF_3)_2$, $O_3SCF_3$, or $O_3SC_4F_9$, methyl sulfate, and/or hydroxide.

The polymerized product of one or more additional monomers may be included in the cationic polymers. Such additional monomers are not particularly limited by structure, but exclude monomers having anionic functionality. Non-limiting examples of additional monomers are N-vinyl pyrrolidone, isobutyl(meth)acrylate, n-butyl(meth)acrylate, isopropyl(meth)acrylate, n-propyl(meth)acrylate, methyl (meth)acrylate, ethyl(meth)acrylate, vinyl acetate, hydroxyethyl(meth)acrylate, hydroxypropyl(meth)acrylate, octadecyl(meth)acrylate, stearyl(meth)acrylate, dimethyl acrylamide, N-(hydroxymethyl)-acrylamide, dimethylaminoethyl(meth)acrylate, methoxy polyethylene glycol(meth)acrylate, polydimethylsiloxane(meth)acrylate), KF 2001 (mercapto modified dimethylsiloxane), perfluorobutyl sulfonamido n-methyl ethyl acrylate, and hexafluoropropylene oxide oligomer amidol(meth)acrylate.

Similarly, in embodiments, the polymerized product of one or more additional monomers is included in the zwitterionic polymers of the invention. Such additional monomers are not particularly limited by structure and include, in some embodiments, anionic functional monomers. Non-limiting examples of additional monomers are isobutyl acrylate, isobutyl methacrylate, n-butyl acrylate, n-butyl methacrylate, isopropyl acrylate, isopropyl methacrylate, n-propyl acrylate, n-propyl methacrylate, methyl acrylate, methyl methacrylate, ethyl acrylate, ethyl methacrylate, vinyl acetate, N-vinyl pyrrolidone, hydroxyethyl acrylate, or hydroxyethyl methacrylate. In some embodiments, the additional monomer is a mixture of two or more of these monomers. In some such embodiments, the additional monomer is vinyl acetate, N-vinyl pyrrolidone, isobutyl acrylate, a mixture of vinyl acetate and N-vinyl pyrrolidone, a mixture of vinyl acetate and isobutyl acrylate, or a mixture of isobutyl acrylate and N-vinyl pyrrolidone.

In some embodiments, the additional monomer has two or more polymerizable functionalities; such monomers are referred to as crosslinkers. Crosslinkers that are useful in forming the cationic or zwitterionic polymers include, without limitation, diacrylates such as ethylene glycol diacrylate, hexanediol diacrylate, and tripropyleneglycol diacrylate; triacrylates such as glycerol triacrylate and trimethylolpropane triacrylate; and tetraacrylates such as erythritol tetraacrylate and pentaerythritol tetraacrylate; divinyl benzene and derivatives thereof, and the like. In some embodiments, the crosslinker is a photoactive crosslinker. Photoactive crosslinkers include, for example, benzaldehyde, acetaldehyde, anthraquinone, substituted anthraquinones, various benzophenone-type compounds and certain chromophore-substituted vinylhalomethyl-s-triazines, such as 2,4-bis(trichloromethyl)-6-p-methoxystyryl-s-triazine. The polymer is included in the printable composition in an amount of 1 to 50 wt. %, inclusive, based on the total weight of the printable composition, such as 25 to 50 wt. %, inclusive. Typically, the polymer is included in the printable composition in an amount of 1 wt. % or more, 2 wt. % or more, 5 wt. % or more, 7 wt. % or more, 10 wt. % or more, 12 wt. % or more, 15 wt. % or more, 20 wt. % or more, or 25 wt % or more; and 50 wt. % or less, 45 wt. % or less, 40 wt. % or less, 35 wt. % or less, or 30 wt. % or less, based on the total weight of the printable composition.

Polymerizable Component

The printable compositions of the present disclosure include at least one polymerizable component. A "polymerizable component," for reference purposes herein, comprises a hardenable component that can be cured to provide a printed article. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used.

Suitable polymerizable components contain at least one ethylenically unsaturated bond, and are capable of undergoing addition polymerization. Such free-radically polymerizable materials include mono-, di-, tri-, or other polyacrylates and methacrylates such as methyl acrylate, methyl methacrylate, ethyl acrylate, isopropyl methacrylate, n-hexyl acrylate, stearyl acrylate, allyl acrylate, glycerol diacrylate, the diurethane dimethacrylate called UDMA (mixture of isomers, e.g., Röhm Plex 6661-0) being the reaction product of 2-hydroxyethyl methacrylate (HEMA) and 2,2,4-trimethylhexamethylene diisocyanate (TMDI), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylme thane, bis[1-(3-acryloxy-2-hydroxy)]-p-propoxyphenyl-dimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); polyfunctional (meth)acrylates comprising urethane, urea or amide groups, as those of EP2008636 (Hecht et al.). The polymerizable component optionally includes urethane groups, epoxy groups, or both. The polymerizable component also may comprise silicone acrylate oligomers, epoxy (meth)acrylate oligomers, polyester (meth)acrylate oligomers or chlorinated polyester (meth)acrylates, allylic oligomers and (meth)acrylic oligomers. Mixtures of two or more of these free radically polymerizable materials can be used if desired.

The polymerizable component preferably comprises one or more poly(meth)acrylates, for example, di-, tri-, tetra- or pentafunctional monomeric or oligomeric aliphatic, cycloaliphatic or aromatic acrylates or methacrylates. For example, the polymerizable component can include polyfunctional urethane acrylates or urethane methacrylates. These urethane (meth)acrylates are known to the person skilled in the art and can be prepared in a known manner by, for example, reacting a hydroxyl-terminated polyurethane with acrylic acid or methacrylic acid, or by reacting an isocyanate-terminated prepolymer with hydroxyalkyl (meth)acrylates to give the urethane (meth)acrylate. Suitable processes are disclosed, inter alia, in U.S. Pat. No. 8,329,776 (Hecht et al.) and U.S. Pat. No. 9,295,617 (Cub et al.). Suitable urethane methacrylates can include PEGDMA (polyethyleneglycol dimethacrylate having a molecular weight of approximately 400), aliphatic urethane methacrylates, aliphatic polyester urethane methacrylates, aliphatic polyester triurethane acrylates.

Examples of suitable aliphatic poly(meth)acrylates having more than two (meth)acrylate groups in their molecules are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate.

Another suitable class of free radical polymerizable compounds includes aromatic di(meth) acrylate compounds and trifunctional or higher functionality (meth) acrylate compound. Trifunctional or higher functionality meth(acrylates) can be tri-, tetra- or pentafunctional monomeric or oligomeric aliphatic, cycloaliphatic or aromatic acrylates or methacrylates.

Examples of suitable aliphatic tri-, tetra- and pentafunctional (meth)acrylates are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate. Further examples of suitable aromatic tri(meth)acrylates are the reaction products of triglycidyl ethers of trihydroxy benzene and phenol or cresol novolaks containing three hydroxyl groups, with (meth)acrylic acid.

In some cases, a polymerizable component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis(4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. In some cases, a polymerizable component of a printable composition described herein comprises one or more higher functional acrylates or methacrylates such as dipentaerythritol monohydroxy pentaacrylate or bis(trimethylolpropane)tetraacrylate.

In certain embodiments, the polymerizable component has a molecular weight of 10,000 grams per mole or less, 9,000 g/mol or less, 8,000 g/mol or less, 7,000 g/mol or less, 6,000 g/mol or less, or 5,000 g/mol or less. Including a polymerizable component with such molecular weights can assist in providing a printable composition that has a sufficiently low viscosity for use with vat polymerization methods. Moreover, using a polymerizable component (e.g., monomer and/or oligomer) with a low molecular weight increases the ease with which the polymerizable component can interpenetrate the polymer in solution to provide an integral article upon polymerization of the polymerizable component. Further, in select embodiments the polymerizable component is soluble or dispersable in water.

The polymerizable component is included in the printable composition in an amount of 5 to 50 wt. %, inclusive, based on the total weight of the printable composition, such as 5 to 25 wt. %, inclusive. Typically, the polymerizable component is included in the printable composition in an amount of 5 wt. % or more, 7 wt. % or more, 5 wt. % or more, 10 wt. % or more, 12 wt. % or more, or 15 wt. % or more; and 50 wt. % or less, 45 wt. % or less, 40 wt. % or less, 35 wt. % or less, 30 wt. % or less, 25 wt. % or less, or 20 wt. % or less, based on the total weight of the printable composition.

Temporary Solvent

The viscosity of the polymerizable component can be significantly reduced by diluting the component in a solvent, such as a nonreactive solvent. As used herein, a "nonreactive solvent" is a solvent that does not polymerize into the printable resin (e.g., the poly(meth)acrylate, initiator, and optionally other additives such as filler). As the solvent is usually nonreactive, it can be extracted from a printed article according to methods discussed below without deleteriously affecting the material properties of the, e.g., high viscosity polymerizable component resin. Accordingly, solvents useful in the present disclosure are referred to herein as temporary solvents.

In certain embodiments, the temporary solvent is advantageously water, an inexpensive and environmentally friendly solvent. Alternatively, the temporary solvent may be an organic solvent having a boiling point of at least 50° C. The boiling point is often at least 100° C., at least 200° C., and typically no greater than 300° C. Suitable temporary solvent are typically non-volatile at ambient temperatures (20-25° C.) and have vapor pressures below about 150.0 hPa at 20° C. (preferably, below about 15.0 hPa at 20° C.; more preferably, below about 1.5 hPa at 20° C.; most preferably, below about 0.15 hPa at 20° C.). Temporary solvents demonstrating the above properties can typically be retained in the printable composition during the printing process even at elevated temperatures, yet be removed from the printed article using conventional techniques such as vacuum assisted evaporation.

In presently preferred implementations, the temporary solvent can include one or more of water, propylene carbonate, methanol, isopropyl alcohol, and tripropylene glycol methyl ether (TPM), ethanol, acetone, ethyl acetate, methyl ethyl ketone, and mixtures thereof.

The temporary solvent is included in the printable composition in an amount of 10 to 80 wt. %, inclusive, based on the total weight of the printable composition, such as 25 to 60 wt. %, inclusive. Typically, the polymerizable component is included in the printable composition in an amount of 10 wt. % or more, 12 wt. % or more, 15 wt. % or more, 17 wt. % or more, 20 wt. % or more, 22 wt. % or more, or 25 wt. % or more; and 80 wt. % or less, 75 wt. % or less, 70 wt. % or less, 65 wt. % or less, 60 wt. % or less, 55 wt. % or less, or 50 wt. % or less, based on the total weight of the printable composition. Under certain conditions, a printable composition having less than 10 wt. % temporary solvent may not have a viscosity suitable for vat polymerization, in that the viscosity of polymerizable component is not adequately low. Conversely, a printable composition including more than 80 wt. % temporary solvent can, under certain conditions, result in green bodies with insufficient green strength and may result in difficulties in adequately removing the temporary solvent from the printed article.

Emulsifiers

In certain embodiments, an emulsion is formed containing the polymer and polymerizable component. The emulsion is a water-in-oil or an oil-in-water emulsion. In some such embodiments, the emulsion is an oil-in-water emulsion, wherein the polymer and/or polymerizable components are stabilized in a bulk water phase by employing one or more emulsifiers (e.g., surfactants). In various embodiments, the emulsifier is cationic, anionic, zwitterionic, or non-ionic in nature and the structure thereof is not otherwise particularly limited. In some embodiments, the emulsifier is a monomer and becomes incorporated within the polymer molecules formed from the polymerizable component. In other embodiments, the emulsifier is present in the polymerization reaction vessel but is not incorporated into the polymer molecules as a result of the polymerization reaction.

Non-limiting examples of anionic emulsifiers useful in forming oil-in-water emulsions include ammonium, sodium, lithium, or potassium salts of lauryl sulfonic acid, dioctyl sodium sulfosuccinic acid, ammonium, sodium, lithium, or potassium salts of perfluorobutanesulfonic acid, ammonium, sodium, lithium, or potassium salts of perfluorooctanesulfonic acid, ammonium, sodium, lithium, or potassium salts of perfluorooctanoic acid, sodium dodecyl sulfate, sodium dodecylbenzenesulfonate, sodium laureth sulfate, sodium lauroyl sarcosinate, sodium myreth sulfate, sodium pareth sulfate, ammonium, sodium, lithium, or potassium salts of stearic acid, and combinations of one or more thereof.

Non-limiting examples of non-ionic emulsifiers useful in forming oil-in-water emulsions include block copolymers of ethylene oxide and propylene oxide, such as those sold under the trade names PLURONIC, KOLLIPHOR, or TETRONIC, by the BASF Corporation of Charlotte, N.C.; ethoxylates formed by the reaction of ethylene oxide with a fatty alcohol, nonylphenol, dodecyl alcohol, and the like, including those sold under the trade name TRITON, by the Dow Chemical Company of Midland, Mich.; oleyl alcohol; sorbitan esters; alkylpolyglycosides such as decyl glucoside; sorbitan tristearate; and combinations of one or more thereof. In select embodiments, a suitable emulsifier comprises one or more non-ionic emulsifiers selected from ethoxylated alcohols, ethoxylated amines, amine oxides, and combinations thereof.

Non-limiting examples of cationic emulsifiers useful in forming oil-in-water emulsions include benzalkonium chloride, cetrimonium bromide, demethyldioctadecylammonium chloride, lauryl methyl gluceth-10 hydroxypropyl diammonium chloride, tetramethylammonium hydroxide, monoalkyltrimethylammonium chlorides, monoalkyldimethylbenzylammonium chlorides, dialkylethylmethylammonium ethosulfates, trialkylmethylammonium chlorides, polyoxyethylenemonoalkylmethylammonium chlorides, and diquaternaryammonium chlorides; the ammonium functional emulsifiers sold by Akzo Nobel N.V. of Amsterdam, the Netherlands, under the trade names ETHOQUAD, ARQUAD, and DUOQUAD; and mixtures thereof. Of particular use in forming oil-in-water emulsions are the ETHOQUAD surfactants, for example, ETHOQUAD C/12, C/25, C/12-75, and the like.

Where a cationic emulsifier is employed in an oil-in-water emulsion polymerization reaction, it is employed in an amount of about 1.0 wt. % to 6.0 wt. % based on the total weight of the monomers, or at about 2.0 wt. % to 4.0 wt. % of the monomers, or in various intermediate levels such as 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2.1 wt. %, 2.2 wt. %, and all other such individual values represented by 0.1 wt. % increments between 1.0 and 6.0 wt. %, and in any range spanning these individual values in 0.1 wt. % increments, such as 2.3 wt. % to 4.6 wt. %, 4.5 wt. % to 4.7 w.t %, and the like.

Additives

Printable compositions described herein, in some instances, further comprise one or more additives, such as one or more additives selected from the group consisting of photoinitiators, inhibitors, stabilizing agents, sensitizers, absorption modifiers, fillers and combinations thereof.

For example, the printable composition further comprises one or more photoinitiators. Suitable exemplary photoinitiators are those available under the trade designations IRGACURE and DAROCUR from BASF (Ludwigshafen, Germany) and include 1-hydroxycyclohexyl phenyl ketone (IRGACURE 184), 2,2-dimethoxy-1,2-diphenylethan-1-one (IRGACURE 651), bis(2,4,6 trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), Oligo[2-hydroxy-2-methyl-1-[4-(1-methylvinyl)phenyl] propanone] ESACURE ONE (Lamberti S.p.A., Gallarate, Italy), 2-hydroxy-2-methyl-1-phenyl propan-1-one (DAROCUR 1173), 2, 4, 6-trimethylbenzoyldiphenylphosphine oxide (IRGACURE TPO), and 2, 4, 6-trimethylbenzoylphenyl phosphinate (IRGACURE TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

A photoinitiator can be present in a printable composition described herein in any amount according to the particular constraints of the additive manufacturing process. In some embodiments, a photoinitiator is present in a printable composition in an amount of up to about 5% by weight, based on the total weight of the printable composition. In some cases, a photoinitiator is present in an amount of about 0.1-5% by weight, based on the total weight of the printable composition.

In addition, a printable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the printable composition, a sensitizer can be present in an amount ranging of about 0.01% by weight or about 1% by weight, based on the total weight of the printable composition.

A printable composition described herein optionally also comprises one or more polymerization inhibitors or stabilizing agents. A polymerization inhibitor is often included in a printable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the printable composition. Further, if used, a stabilizing agent is present in a printable composition described herein in an amount of about 0.1-5% by weight, about 0.5-4% by weight, or about 1-3% by weight, based on the total weight of the printable composition.

A printable composition as described herein can also comprise one or more absorption modifiers (e.g., dyes, optical brighteners, pigments, particulate fillers, etc.) to control the penetration depth of actinic radiation. One particularly suitable absorption modifier is Tinopal OB, a benzoxazole, 2,2'-(2,5-thiophenediyl)bis[5-(1,1-dimethylethyl)], available from BASF Corporation, Florham Park, N.J. The absorption modifier, if used, can be present in an amount of about 0.001-5% by weight, about 0.01-1% by weight, about 0.1-3% by weight, or about 0.1-1% by weight, based on the total weight of the printable composition.

Printable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, Ohio and CAB-O-SIL M5 and TS-720 silica from Cabot Corp., Tuscola, Ill.). Organic fillers made from polymeric materials are also possible, such as those disclosed in International Publication No. WO09/045752 (Kalgutkar et al.).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, Minn.), such as NEXTEL 312, 440, 610 and 720. One presently preferred ceramic fiber comprises polycrystalline $\alpha$-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, Minn.). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, Minn.). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the printed compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Printable compositions materials herein can also exhibit a variety of desirable properties, non-cured, as green bodies, and as post-cured articles. A printable composition, when non-cured, has a viscosity profile consistent with the requirements and parameters of one or more 3D printing systems. In some instances, a printable composition described herein when non-cured exhibits a dynamic viscosity of about 0.1-15,000 cP, about 100-10,000 cP, or about 200-5,000 cP at 25 degrees Celsius using a #1 spindle, when measured according to ASTM D4287, as set forth in the Example Test Method below. In some cases, a printable composition described herein when non-cured exhibits a dynamic viscosity of less than about 100 cP or more than about 1000 cP, when measured according to modified ASTM D4287.

Articles and Methods

In a second aspect, the present disclosure provides an article. The article comprises an integral blend of 8 to 50 wt. %, inclusive, of a thermoset polymer and 30 to 90 wt. %, inclusive, of a second polymer different from the thermoset polymer, wherein the weight percent is based on the total weight of the article. The second polymer optionally comprises an uncrosslinked polymer. In many embodiments, the thermoset polymer of the article is vat polymerized, as discussed in detail below.

The shape of the article is not limited, and may comprise a film or a shaped integral article. For instance, a film may readily be prepared by casting the printable composition according to the first aspect, then subjecting the cast composition to actinic radiation to polymerize the polymerizable composition. In many embodiments, the article comprises a shaped integral article, in which more than one variation in dimension is provided by a single integral article. For example, the article can comprise one or more channels, one or more undercuts, one or more perforations, or combinations thereof. Such features are not possible to provide in an integral article using conventional molding methods.

In select embodiments, the article comprises an orthodontic article. Orthodontic articles are described in further detail below. Use of the integral blend of the thermoset polymer and second polymer often provides desirable physical properties from each of the two polymers, such as strength (e.g., from the thermoset polymer) as well as flexibility (e.g., from the second polymer).

An advantage of employing additive manufacturing processes such as stereolithography or vat polymerization is that an article can be formed with a relatively low void content (e.g., empty spaces disposed within the polymeric material). In some embodiments, the article comprises a void content of ranging from 0.1 to 1.5%, inclusive, or ranging from 2.0 to 5.5%, inclusive. Such low void contents may provide benefits with respect to tensile strength of the article.

In a third aspect, the present disclosure provides a method of making an article. The method comprises:

(i) providing a printable composition comprising: (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition;

(ii) selectively curing the printable composition to form a gelled article;

(iii) removing at least a portion of the temporary solvent from the gelled article; and (iv) optionally curing unpolymerized polymerizable component remaining before or after step (iii).

In additive manufacturing methods, the method further comprises (v) repeating steps (i) and (ii) to form multiple layers and create the gelled article comprising a three dimensional structure prior to step (iii).

A printable composition described herein in a cured state, in some embodiments, can exhibit one or more desired properties. A printable composition in a "cured" state can comprise a printable composition that includes a polymerizable component that has been at least partially polymerized and/or crosslinked. For instance, in some instances, a cured article is at least about 10% polymerized or crosslinked or at least about 30% polymerized or crosslinked. In some cases, a cured printable composition is at least about 50%, at least about 70%, at least about 80%, or at least about 90% polymerized or crosslinked. A cured printable composition can also be between about 10% and about 99% polymerized or crosslinked.

The conformability and durability of a cured article made from the printable compositions of the present disclosure can be determined in part by standard tensile and elongation testing. The printable compositions can typically be characterized by at least one of the following parameters after hardening. The elongation at break is typically 40% or greater, 50% or greater, 75% or greater, 100% or greater, 125% or greater, 150% or greater, or 200% or greater; and 600% or less, 500% or less, 400% or less, 300% or less, or 250% or less. Stated another way, the elongation at break of the cured article can range from 40% to 600%. In some embodiments, the elongation at break is at least 50% and no greater than 500%. The ultimate tensile strength is typically at least 2, 3, or 4 MPa and is typically no greater than 80 MPa. Such tensile and elongation properties can be measured, for example, by the methods outlined in ASTM D638-10, using test specimen Type V. The mechanical properties above are particularly well suited for articles that require resiliency and flexibility, along with adequate wear strength and low hygroscopicity.

Printable compositions described herein can be mixed by known techniques. In some embodiments, for instance, a method for the preparation of a printable composition described herein comprises the steps of mixing all or substantially all of the components of the printable composition, heating the mixture, and optionally filtering the heated mixture. Softening the mixture, in some embodiments, is carried out at a temperature of about 50° C. or in a range from about 50° C. to about 85° C. In some embodiments, a printable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

Fabricating an Article

Once prepared as set forth above, the printable compositions of the present disclosure may be used in myriad additive manufacturing processes to create a variety of articles, including casting a film as noted above. A generalized method 100 for creating three-dimensional articles is illustrated in FIG. 1. Each step in the method will be discussed in greater detail below. First, in Step 110 the desired printable composition is provided and introduced into a reservoir, cartridge, or other suitable container for use by or in a 3D printer. The 3D printer selectively cures the printed composition according to a set of computerized design instructions in Step 120 to create a gelled article representing the desired article. Once the initial curing process in complete, the temporary solvent is removed from the cured article in Step 130 via heating, solvent extraction, or other methods for removing solvent known in the art. Following the solvent removal processes of Step 130, the gelled article is subjected to additional curing to polymerize remaining uncured polymerizable components in the gelled article in Step 140.

Methods of printing a three dimensional article or object described herein can include forming the article from a plurality of layers of a printable composition described herein in a layer-by-layer manner. Further, the layers of a build material composition can be deposited according to an image of the three dimensional article in a computer readable format. In some or all embodiments, the printable composition is deposited according to preselected computer aided design (CAD) parameters.

Additionally, it is to be understood that methods of printing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with printable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a printable composition described herein using stereolithography (e.g., vat polymerization). For example, in some cases, a method of printing a 3D article comprises retaining a printable composition described herein in a fluid state in a container and selectively applying energy to the printable composition in the container to solidify at least a portion of a fluid layer of the printable composition, thereby forming a hardened layer that defines a cross-section of the 3D article. Additionally, a method described herein can further comprise raising or lowering the hardened layer of printable composition to provide a new or second fluid layer of unhardened printable composition at the surface of the fluid in the container, followed by again selectively applying energy to the printable composition in the container to solidify at least a portion of the new or second fluid layer of the printable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the printable composition. Moreover, selectively applying energy to the printable composition in the container can comprise applying actinic radiation, such as UV radiation, visible radiation, or e-beam radiation, having a sufficient energy to cure the printable composition. A method described herein can also comprise planarizing a new layer of fluid printable composition provided by raising or lowering an elevator platform. Such planarization can be carried out, in some cases, by utilizing a wiper or roller or a recoater bead. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of printable composition, can be carried out according to an image of the 3D article in a computer-readable format. Suitable stereolithography printers include the Viper Pro SLA, available from 3D Systems, Rock Hill, S.C. and the Asiga Pico Plus39, available from Asiga USA, Anaheim Hills, Calif.

Figure 2:
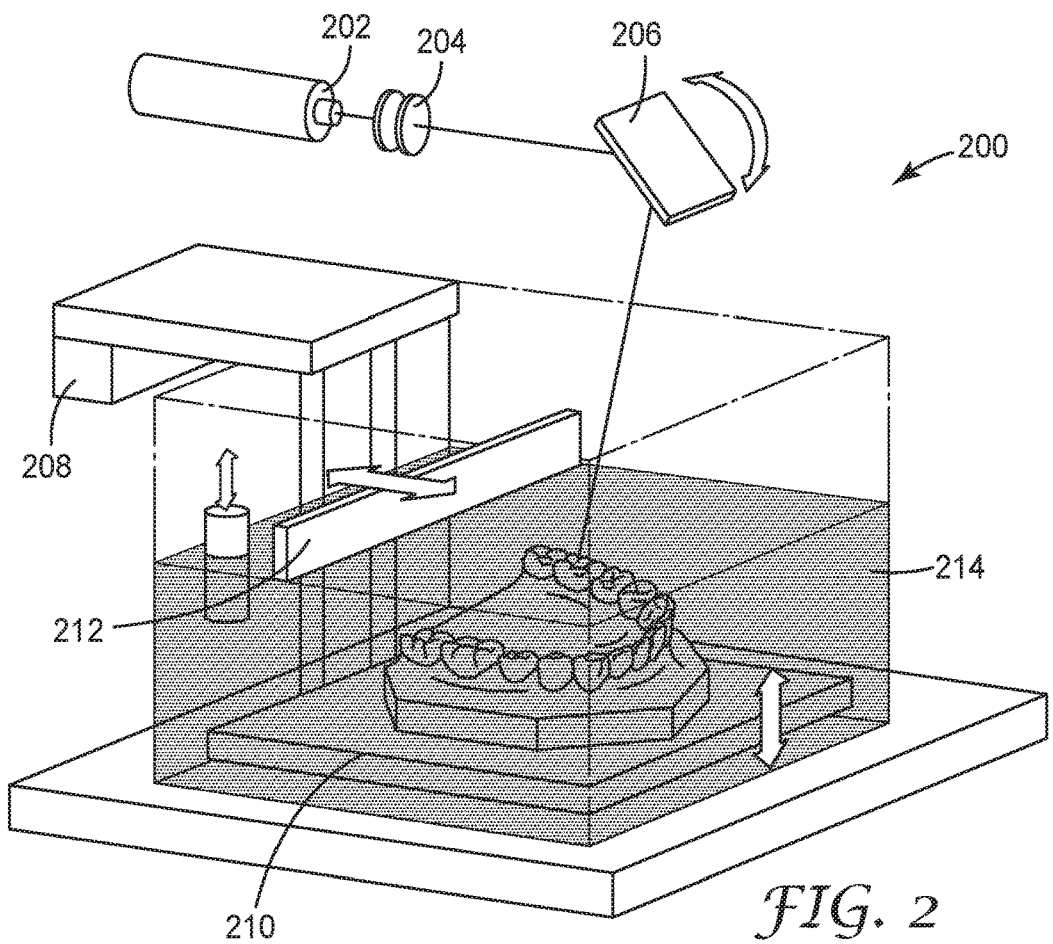
FIG. 2 is a generalized schematic of a stereo lithography apparatus.

FIG. 2 shows an exemplary stereo lithography apparatus ("SLA") that may be used with the printable compositions and methods described herein. In general, the SLA 200 may include a laser 202, optics 204, a steering lens 206, an elevator 208, a platform 210, and a straight edge 212, within a vat 214 filled with the printable composition. In operation, the laser 202 is steered across a surface of the printable composition to cure a cross-section of the printable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the printable composition.

A related technology, vat polymerization with Digital Light Processing ("DLP"), also employs a container of curable polymer (e.g., printable composition). However, in a DLP based system, a two-dimensional cross section is projected onto the curable material to cure the desired section of an entire plane transverse to the projected beam at one time. All such curable polymer systems as may be adapted to use with the printable compositions described herein are intended to fall within the scope of the term "stereolithography system" as used herein.

More generally, the printable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the 3D printing apparatus and rinsed, (e.g., an ultrasonic, or bubbling, or spray rinse in a solvent (which may be the same as or different from the temporary solvent in the printable composition) which would dissolve a portion of the uncured printable composition but not the cured, solid state gelled article (e.g., green body). Any other conventional method for cleaning the article and removing uncured material at the article surface may also be utilized. At this stage, the three-dimensional article typically has sufficient green strength for handling in the remaining steps of method 100.

Turning back to FIG. 1, the temporary solvent is substantially removed from the gelled article in Step 130. In presently preferred implementations, the removal of the temporary solvent occurs prior to any postcure processing in Step 140. Alternatively, the temporary solvent may be removed after or during postcure. Any known means for solvent removal can be used. The gelled article can be subjected, for example, to at least one of ambient conditions, oven drying, vacuum pressurization (e.g., under a vacuum), solvent exchange, or any combination thereof. The temporary solvent may be removed from the gelled article using heat sources such as a hot air gun, hot plate, steam, conventional oven, infrared heater, radiofrequency (RF) sources or microwave sources. In some embodiments, the cured article is heated to a temperature above room temperature, for example, about 60° C., during the solvent removal process of Step 130. However, various temperatures and times may be utilized.

In some embodiments, the solvent is removed according to an oven-drying process. For example, the article can be dried in a conventional oven at a temperature equal to at least 30° C., at least 40° C., at least 60° C., at least 70° C. The drying time is often greater than 6 hours, greater than 12 hours, greater than 24 hours or greater than 36 hours. In some or all embodiments, the temperature is gradually increased in the oven. For example, the rate of temperature increase could be in the range of about 0.5° C. to about 10° C. per minute. In presently preferred implementations, the temperature is increased in step-wise fashion, with at least 10 minutes of dwell time at a given temperature between temperature increases.

Alternatively, the article can be immersed in a heated bath containing a suitable inert liquid (for example, water) that will not dissolve or distort the article. Furthermore, the inert liquid will typically have a lower boiling point than the temporary solvent, so that the inert liquid can be more easily removed from the gelled article. In one such solvent exchange implementation of temporary solvent removal, the gelled article can be immersed in the liquid bath for 24 to 48 hours, at a temperature of 33° C., for example. Upon removal, the gelled article can be allowed to dry at room temperature (about 20-25° C.) for up to 48 hours. However, various temperatures and times may be utilized to reduce or increase the dry time, immersion time, and combinations thereof.

The above techniques for solvent removal may be combined with vacuum pressure to enhance the evaporation of the temporary solvent from the cured article. In some embodiments, the vacuum pressure applied is no greater than 500 hPa, in some embodiments no greater than 200 hPa, in some embodiments no greater than 100 hPa, and in yet other embodiments less than 20 hPa. In certain circumstances, the solvent removal may be performed at vacuum pressures of 1 hPa or lower. The rate of vacuum pressure increase is typically selected to avoid boiling of the temporary solvent in the gelled article, which can introduce foamed regions into the shaped article.

In some or all embodiments, a substantial portion of the temporary solvent is removed from the gelled article. Allowing excess temporary solvent to remain in the printed article can deleteriously affect the otherwise desirable properties of the cured material, depending on the particular application and resin composition. In presently preferred implementations, at least 60 percent of the temporary solvent is removed. In other implementations, at least 80 percent, at least 90 percent, at least 95 percent, at least 98 percent, and at least 99 percent of the temporary solvent is removed from the three-dimensional article. The percent of solvent removal can be confirmed by recording the mass of the article before and after curing. In certain embodiments, particularly those with relatively high temporary solvent levels, some portion of the temporary solvent may be removed during the initial 3D printing process. Accordingly, the amount of temporary solvent removed during the subsequent solvent removal step will be less than expected given the concentration of solvent in the relevant printable composition.

In certain implementations, allowing an amount of temporary solvent to remain in the article can be acceptable, as this may shorten process and manufacturing times, particularly when the concentration of temporary solvent in the printable resin is low prior to printing. Furthermore, the presence of acceptable amounts of temporary solvent may result in a softer three-dimensional article, which may be advantageous in certain implementations.

Due in part to the removal of the temporary solvent, it is expected in certain embodiments of the present disclosure that the printed article obtained in Step 120 will shrink (i.e., reduce in volume) such that the dimensions of the article after Step 130 will be smaller than expected. For example, a printed article may shrink about 6-8% in volume upon solvent removal, though this will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 105%, in some embodiments, at least 110%, and in some embodiments, at least 120%.

A global scale factor may be calculated for any given printable composition formulation by creating a calibration part according to Steps 210 and 220 above. The dimensions of the calibration article can be measured prior to the solvent removal of Step 230 and postcure of Step 240.

In general, the three-dimensional article formed by initial 3D printing step in Step 120, as discussed above, is not fully cured, by which is meant that not all of the polymerizable material in the composition has polymerized even after rinsing and solvent removal. Some uncured polymerizable material is typically removed from the surface of the printed article during a cleaning process preceding the temporary solvent removal of Step 130. The article surface, as well as the bulk article itself, typically still retains uncured polymerizable material, suggesting further cure. Removing residual uncured printable composition is particularly useful when the gelled article is going to subsequently be post-cured, to minimize uncured residual printable composition from undesirably curing directly onto the gelled article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure process of Step 140. In general, postcuring improves the mechanical properties and stability of the three-dimensional article relative to the gelled article.

In select embodiments, the method optionally comprises heating the gelled article to within 10 degrees Celsius of the glass transition temperature ($T_g$) of the second polymer for a time of at least 5 minutes. It has been unexpectedly discovered that such heating of the gelled article relaxes the polymeric chains in the article to decrease internal strains without loss of the printed shape of the gelled article.

The following describes general methods for creating a clear tray aligner as printed appliance 400. However, other dental and orthodontic articles can be created using similar techniques and the printable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the printable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other printable orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

Alternatively, the printable compositions can be used in other industries, such as aerospace, animation and entertainment, architecture and art, automotive, consumer goods and packaging, education, electronics, hearing aids, sporting goods, jewelry, medical, manufacturing, etc.

As another alternative example, it is possible in this context to use the printable compositions as adhesives or as coating compositions. When the novel mixtures are employed as coating compositions, the resulting coatings on wood, paper, metal, ceramic, polymer, or other surfaces can be scratch resistant, and possess other desirable qualities depending on the application. The printable compositions described herein can be used to form a (e.g., cured) surface layer, a coated article, or a coated surface such as by applying the coating composition to a surface (e.g., of a substrate or article) and curing polymerizable components of the coating composition. Once polymerizable components present in the coating compositions have been cured, a suitable solvent (such as water in some embodiments) can be used to extract the non-reactive temporary solvent from the coated surface or cured coating composition. Accordingly, the printable compositions may be applied as coating compositions to enhance the properties of printed articles and articles fabricated by any other methods.

Fabricating an Orthodontic Appliance with the Printable Compositions

Figure 3:
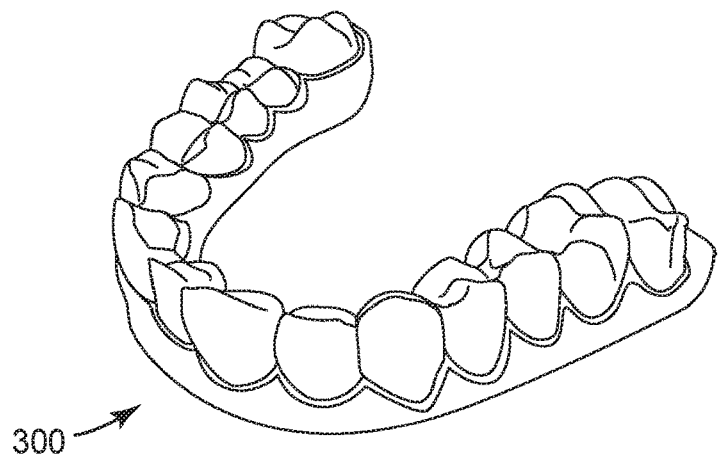
FIG. 3 is an isometric view of a printed clear tray aligner, according to one embodiment of the present disclosure.

One particularly interesting implementation of a printed article is generally depicted in FIG. 3. The printed article 300 is a clear tray aligner and is removably positionable over some or all of a patient's teeth. In some embodiments, printed appliance 300 is one of a plurality of incremental adjustment appliances. The printed appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of receptacles may be misaligned as compared to the corresponding tooth of the patient. In this manner, the appliance body printed appliance 300 may be configured to apply rotational and/or translational forces to the corresponding tooth of the patient when the printed appliance 300 is worn by the patient. In some particular examples, the printed appliance 300 may be configured to provide only compressive or linear forces. In the same or different examples, the printed appliance 300 may be configured to apply translational forces to one or more of the teeth within receptacles.

In some embodiments, the shell of the printed appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. A printed appliance 300 can accordingly be designed such that any receptacle is shaped to facilitate retention of the tooth in a particular position in order to maintain the current position of the tooth.

Figure 4:
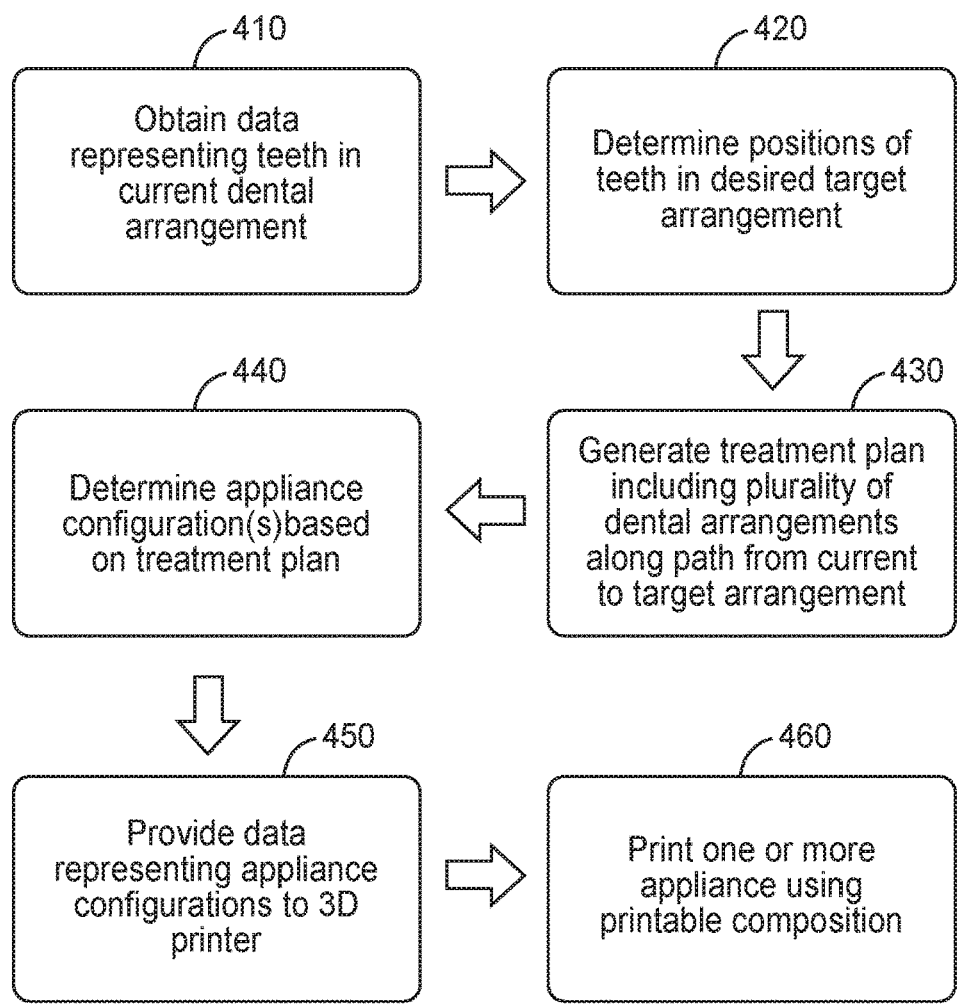
FIG. 4 is a flowchart of a process for manufacturing a printed orthodontic appliance according to the present disclosure.

A method 400 of creating an orthodontic appliance using the printable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to a 3D printer system (Step 450). An appliance can be printed using a printable composition of the present disclosure retained in the 3D printer (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising an integral blend of 8 to 50 wt. %, inclusive, of a thermoset polymer and 30 to 90 wt. %, inclusive, of a second polymer different from the thermoset polymer, wherein the weight percent is based on the total weight of the article. In certain embodiments, the article is an orthodontic article.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In embodiments wherein the article is an orthodontic article, scanning techniques may include, for example, scanning a patient's mouth to customize an orthodontic article for the patient.

Figure 10:
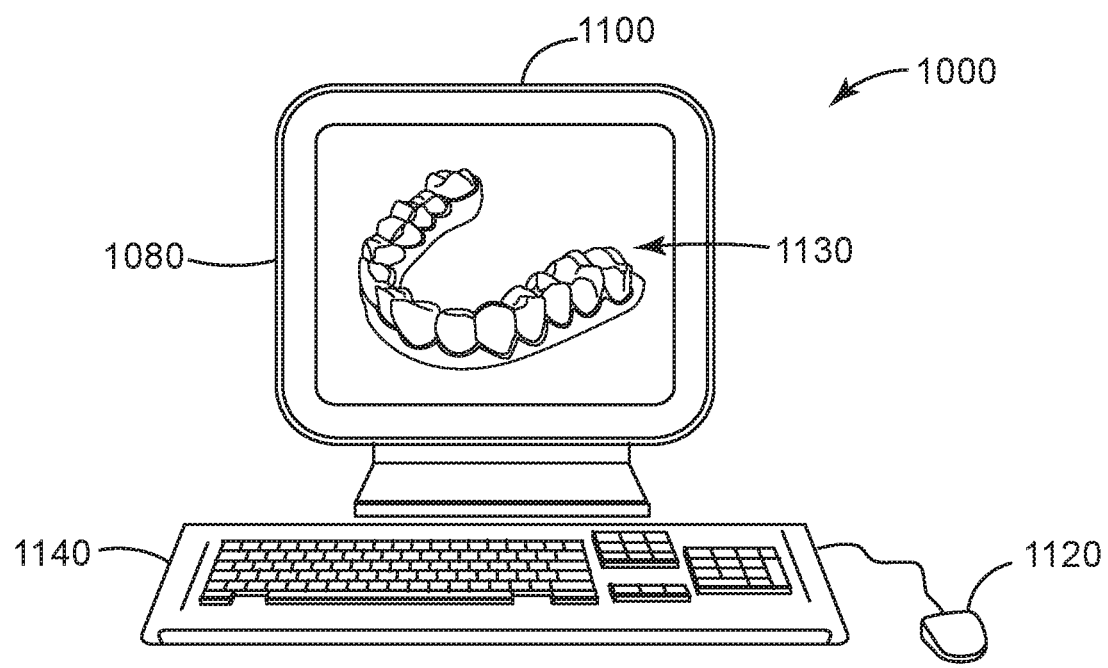
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner 1130 is shown on the display 1100.

Figure 6:
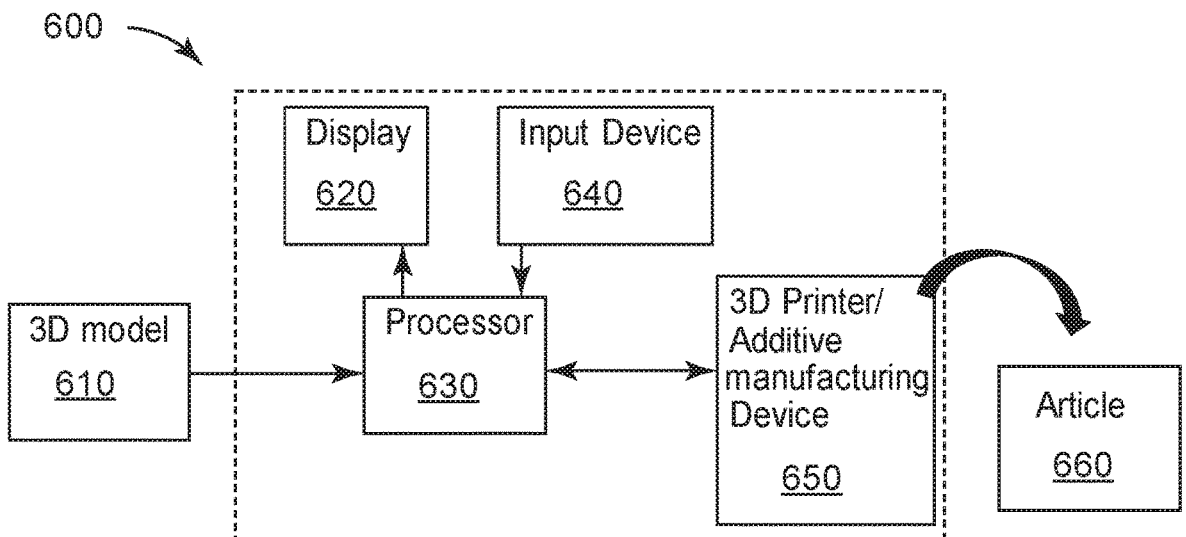
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises an integral blend of 8 to 50 wt. %, inclusive, of a thermoset polymer and 30 to 90 wt. %, inclusive, of a second polymer different from the thermoset polymer, wherein the weight percent is based on the total weight of the article.

Figure 7:
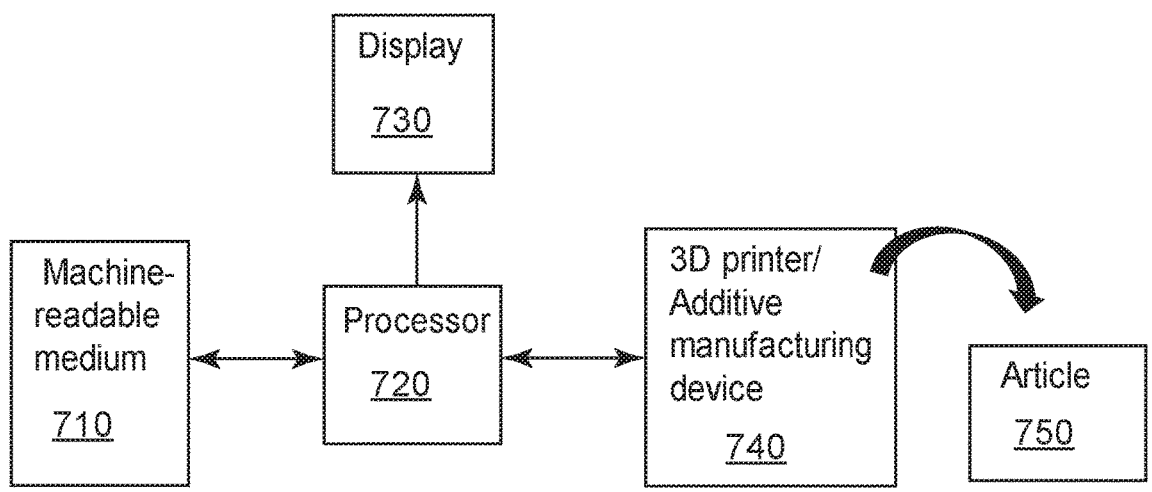
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner 1130 as shown on the display 1100 of FIG. 10) from the machine-readable medium 710.

Figure 8:
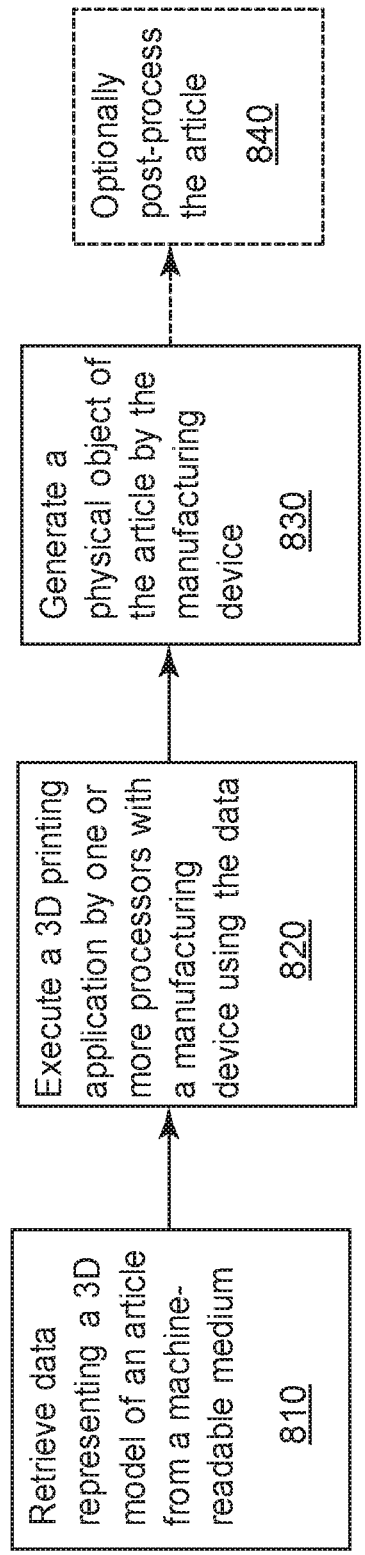
FIG. 8 is a high-level flow chart of an exemplary article manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a printable composition to form a gelled article, wherein the printable composition comprises: (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition. One or more various optional post-processing steps 840 may be undertaken. Typically, next at least a portion of the temporary solvent is removed from the gelled article, and then optionally, the unpolymerized polymerizable component remaining before or after removing temporary solvent may be cured.

Figure 9:
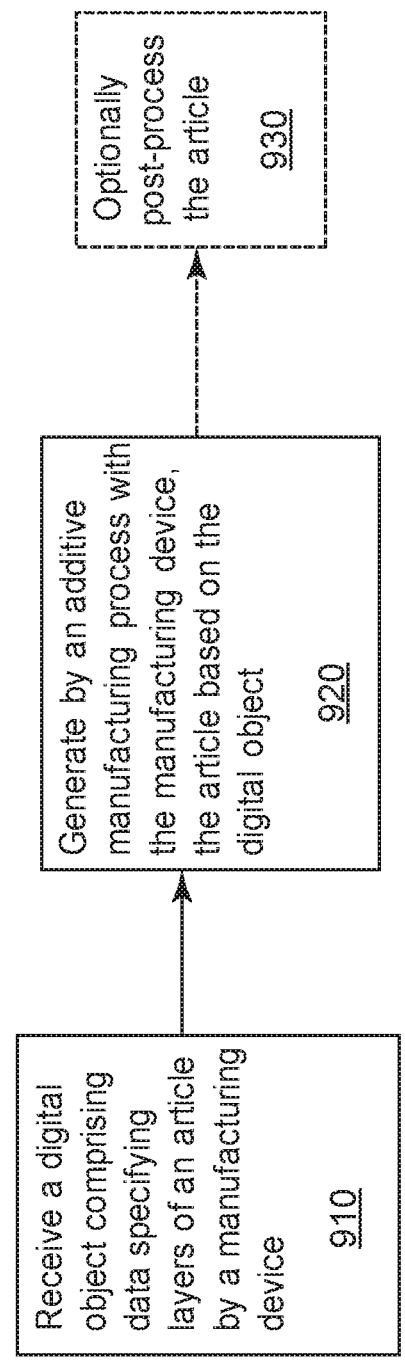
FIG. 9 is a high-level flow chart of an exemplary article additive manufacturing process.

Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930.

Select Embodiments of the Disclosure

Embodiment 1 is a printable composition. The printable composition includes (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition.

Embodiment 2 is the printable composition of embodiment 1, further including 0.01 to 1 wt. %, inclusive, of an absorption modifier.

Embodiment 3 is the printable composition of embodiment 1 or embodiment 2, where the polymer includes a non-crosslinkable polymer.

Embodiment 4 is the printable composition of any of embodiments 1 to 3, where the polymer includes a thermoplastic polymer.

Embodiment 5 is the printable composition of any of embodiments 1 to 4, where the polymer includes one or more functional groups selected from hydroxyl groups, carboxyl groups, amino groups, and siloxane groups.

Embodiment 6 is the printable composition of any of embodiments 1 to 5, where the polymer includes a weight average molecular weight of 20,000 grams per mole or greater.

Embodiment 7 is the printable composition of any of embodiments 1 to 6, where the polymer includes a weight average molecular weight of 100,000 grams per mole or greater.

Embodiment 8 is the printable composition of any of embodiments 1 to 7, where the polymer is selected from the group consisting of polyethylene (PE), poly(meth)acrylate, polypropylene, polyurethane, sulfopolyester, polycarbonate, polyethylene terephthalate (PET), a thermoplastic fluoropolymer, and combinations thereof.

Embodiment 9 is the printable composition of any of embodiments 1 to 8, where the polymer includes poly(meth)acrylate.

Embodiment 10 is the printable composition of any of embodiments 1 to 9, where the polymerizable component includes polymerizable acrylate groups, polymerizable methacrylate groups, or combinations thereof.

Embodiment 11 is the printable composition of any of embodiments 1 to 10, where the polymerizable component includes diacrylates, dimethacrylates, triacrylates, trimethacrylates, acrylates having four or more acrylate groups, methacrylates having four or more methacrylate groups, or combinations thereof.

Embodiment 12 is the printable composition of any of embodiments 1 to 11, where the polymerizable component includes urethane groups.

Embodiment 13 is the printable composition of any of embodiments 1 to 12, where the polymerizable component includes epoxy groups.

Embodiment 14 is the printable composition of any of embodiments 1 to 13, where the polymerizable component has a molecular weight of 10,000 grams per mole or less.

Embodiment 15 is the printable composition of any of embodiments 1 to 14, where the polymerizable component is soluble or dispersable in water.

Embodiment 16 is the printable composition of any of embodiments 1 to 15, further including one or more emulsifiers.

Embodiment 17 is the printable composition of any of embodiments 1 to 16, further including one or more ionic or zwitterionic emulsifiers.

Embodiment 18 is the printable composition of any of embodiments 1 to 17, further including one or more non-ionic emulsifiers selected from ethoxylated alcohols, ethoxylated amines, amine oxides, and combinations thereof.

Embodiment 19 is the printable composition of any of embodiments 1 to 18, where the printable composition has a viscosity of 15,000 cP or less at 25° C. using a #1 spindle.

Embodiment 20 is the printable composition of any of embodiments 1 to 19, where the printable composition has a viscosity of 10,000 cP or less at 25° C. using a #1 spindle.

Embodiment 21 is the printable composition of any of embodiments 1 to 20, where the printable composition has a viscosity of 5,000 cP or less at 25° C. using a #1 spindle.

Embodiment 22 is the printable composition of any of embodiments 1 to 21, where the temporary solvent is nonreactive in the printable composition.

Embodiment 23 is the printable composition of any of embodiments 1 to 22, where the temporary solvent is selected from the group consisting of water, propylene carbonate, methanol, isopropyl alcohol, tripropylene glycol methyl ether, ethanol, acetone, ethyl acetate, methyl ethyl ketone, and combinations thereof.

Embodiment 24 is the printable composition of any of embodiments 1 to 23, further including at least one filler.

Embodiment 25 is the printable composition of any of embodiments 1 to 24, further including at least one filler selected from silica, alumina, zirconia, and discontinuous fibers.

Embodiment 26 is the printable composition of embodiment 25, where the discontinuous fibers include carbon, ceramic, glass, or combinations thereof.

Embodiment 27 is the printable composition of any of embodiments 1 to 26, including 25 to 50 wt. %, inclusive, of the polymer.

Embodiment 28 is the printable composition of any of embodiments 1 to 27, including 5 to 25 wt. %, inclusive, of the polymerizable component.

Embodiment 29 is the printable composition of any of embodiments 1 to 28, including 25 to 60 wt. %, inclusive, of the temporary solvent.

Embodiment 30 is an article. The article includes an integral blend of 8 to 50 wt. %, inclusive, of a thermoset polymer and 30 to 90 wt. %, inclusive, of a second polymer different from the thermoset polymer, where the weight percent is based on the total weight of the article.

Embodiment 31 is the article of embodiment 30, where the thermoset polymer is vat polymerized.

Embodiment 32 is the article of embodiment 30 or embodiment 31, including a film or a shaped integral article.

Embodiment 33 is the article of any of embodiments 30 to 32, including an orthodontic article.

Embodiment 34 is the article of any of embodiments 30 to 33, including one or more channels, one or more undercuts, one or more perforations, or combinations thereof.

Embodiment 35 is the article of any of embodiments 30 to 34, including a void content ranging from 0.1 to 1.5%, inclusive.

Embodiment 36 is the article of any of embodiments 30 to 35, including a void content ranging from 2.0 to 5.5%, inclusive.

Embodiment 37 is the article of any of embodiments 30 to 36, including an elongation extension at break of 50% or greater.

Embodiment 38 is the article of any of embodiments 30 to 37, where the second polymer includes an uncrosslinked polymer.

Embodiment 39 is the article of any of embodiments 30 to 38, where the second polymer includes a thermoplastic polymer.

Embodiment 40 is the article of any of embodiments 30 to 39, where the second polymer includes one or more functional groups selected from hydroxyl groups, carboxyl groups, amino groups, and siloxane groups.

Embodiment 41 is the article of any of embodiments 30 to 40, where the second polymer is selected from the group consisting of polyethylene (PE), poly(meth)acrylate, polypropylene, polyurethane, sulfopolyester, polycarbonate, polyethylene terephthalate (PET), a thermoplastic fluoropolymer, and combinations thereof.

Embodiment 42 is the article of any of embodiments 30 to 41, where the second polymer includes poly(methyl) acrylate.

Embodiment 43 is the article of any of embodiments 30 to 42, where the thermoset polymer includes an acrylate polymer.

Embodiment 44 is the article of any of embodiments 30 to 43, where the thermoset polymer includes urethane groups.

Embodiment 45 is the article of any of embodiments 30 to 44, further including at least one filler.

Embodiment 46 is the article of any of embodiments 30 to 45, further including at least one filler selected from silica, alumina, zirconia, and discontinuous fibers.

Embodiment 47 is the article of embodiment 46, where the discontinuous fibers include carbon, ceramic, glass, or combinations thereof.

Embodiment 48 is a method of making an article. The method includes: (i) providing a printable composition; (ii) selectively curing the printable composition to form a gelled article; and (iii) removing at least a portion of the temporary solvent from the gelled article. The method further includes (iv) optionally curing unpolymerized polymerizable component remaining before or after step (iii). The printable composition includes: (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition.

Embodiment 49 is the method of embodiment 48, further including (v) repeating steps (i) and (ii) to form multiple layers and create the gelled article having a three dimensional structure prior to step (iii).

Embodiment 50 is the method of embodiment 48 or embodiment 49, where the printable composition is cured using actinic radiation.

Embodiment 51 is the method of embodiment 50, where the actinic radiation includes UV radiation, e-beam radiation, visible radiation, or a combination thereof.

Embodiment 52 is the method of any of embodiments 48 to 51, where removing at least a portion of the temporary solvent includes drying in an ambient conditions, in an oven, under vacuum, or combinations thereof.

Embodiment 53 is the method of any of embodiments 48 to 52, further including removing at least a portion of residual uncured printable composition from the gelled article.

Embodiment 54 is the method of any of embodiments 48 to 53, further including postcuring the gelled article using actinic radiation or heat.

Embodiment 55 is the method of any of embodiments 48 to 54, further including heating the gelled article to within 10 degrees Celsius of the $T_g$ of the second polymer for a time of at least 5 minutes.

Embodiment 56 is the method of any of embodiments 48 to 55, where the printable composition further includes 0.01 to 1 wt. %, inclusive, of an absorption modifier.

Embodiment 57 is the method of any of embodiments 48 to 56, where the polymer includes a non-crosslinkable polymer.

Embodiment 58 is the method of any of embodiments 48 to 57, where the polymer includes a thermoplastic polymer.

Embodiment 59 is the method of any of embodiments 48 to 58, where the polymer includes one or more functional groups selected from hydroxyl groups, carboxyl groups, amino groups, and siloxane groups.

Embodiment 60 is the method of any of embodiments 48 to 59, where the polymer includes a weight average molecular weight of 20,000 grams per mole or greater.

Embodiment 61 is the method of any of embodiments 48 to 60, where the polymer comprises a weight average molecular weight of 100,000 grams per mole or greater.

Embodiment 62 is the method of any of embodiments 48 to 61, where the polymer is selected from the group consisting of polyethylene (PE), poly(meth)acrylate, polypropylene, polyurethane, sulfopolyester, polycarbonate, polyethylene terephthalate (PET), a thermoplastic fluoropolymer, and combinations thereof.

Embodiment 63 is the method of any of embodiments 48 to 62, where the polymer includes poly(meth)acrylate.

Embodiment 64 is the method of any of embodiments 48 to 63, where the polymerizable component includes polymerizable acrylate groups, polymerizable methacrylate groups, or combinations thereof.

Embodiment 65 is the method of any of embodiments 48 to 64, where the polymerizable component includes diacrylates, dimethacrylates, triacrylates, trimethacrylates, acrylates having four or more acrylate groups, methacrylates having four or more methacrylate groups, or combinations thereof.

Embodiment 66 is the method of any of embodiments 48 to 65, where the polymerizable component includes urethane groups.

Embodiment 67 is the method of any of embodiments 48 to 66, where the polymerizable component includes epoxy groups.

Embodiment 68 is the method of any of embodiments 48 to 67, where the polymerizable component has a molecular weight of 10,000 grams per mole or less.

Embodiment 69 is the method of any of embodiments 48 to 68, where the polymerizable component is soluble or dispersible in water.

Embodiment 70 is the method of any of embodiments 48 to 69, where the printable composition further includes one or more emulsifiers.

Embodiment 71 is the method of any of embodiments 48 to 70, where the printable composition further includes one or more ionic or zwitterionic emulsifiers.

Embodiment 72 is the method of any of embodiments 48 to 71, where the printable composition further includes one or more non-ionic emulsifiers selected from ethoxylated alcohols, ethoxylated amines, amine oxides, and combinations thereof.

Embodiment 73 is the method of any of embodiments 48 to 72, where the printable composition has a viscosity of 15,000 cP or less at 25° C. using a #1 spindle.

Embodiment 74 is the method of any of embodiments 48 to 73, where the printable composition has a viscosity of 10,000 cP or less at 25° C. using a #1 spindle.

Embodiment 75 is the method of any of embodiments 48 to 74, where the printable composition has a viscosity of 5,000 cP or less at 25° C. using a #1 spindle.

Embodiment 76 is the method of any of embodiments 48 to 75, where the temporary solvent is nonreactive in the printable composition.

Embodiment 77 is the method of any of embodiments 48 to 76, where the temporary solvent is selected from the group consisting of water, propylene carbonate, methanol, isopropyl alcohol, tripropylene glycol methyl ether, ethanol, acetone, ethyl acetate, methyl ethyl ketone, and combinations thereof.

Embodiment 78 is the method of any of embodiments 48 to 77, where the printable composition further includes at least one filler.

Embodiment 79 is the method of any of embodiments 48 to 78, where the printable composition further includes at least one filler selected from silica, alumina, zirconia, and discontinuous fibers.

Embodiment 80 is the method of embodiment 79, where the discontinuous fibers include carbon, ceramic, glass, or combinations thereof.

Embodiment 81 is the method of any of embodiments 48 to 80, where the printable composition includes 25 to 50 wt. %, inclusive, of the polymer.

Embodiment 82 is the method of any of embodiments 48 to 81, where the printable composition includes 5 to 25 wt. %, inclusive, of the polymerizable component.

Embodiment 83 is the method of any of embodiments 48 to 82, where the printable composition includes 25 to 60 wt. %, inclusive, of the temporary solvent.

Embodiment 84 is the method of any of embodiments 48 to 83, where the gelled article includes a film or a shaped integral article.

Embodiment 85 is the method of any of embodiments 48 to 84, where the gelled article is vat polymerized.

Embodiment 86 is the method of any of embodiments 48 to 85, where the gelled article includes an orthodontic article.

Embodiment 87 is the method of any of embodiments 48 to 86, where the gelled article includes one or more channels, one or more undercuts, one or more perforations, or combinations thereof.

Embodiment 88 is the method of any of embodiments 48 to 87, where the gelled article includes a void content ranging from 0.1 to 1.5%, inclusive.

Embodiment 89 is the method of any of embodiments 48 to 88, where the gelled article includes a void content ranging from 2.0 to 5.5%, inclusive.

Embodiment 90 is the method of any of embodiments 48 to 89, where the gelled article includes an elongation extension at break of 50% or greater.

Embodiment 91 is the method of any of embodiments 48 to 90, where the polymer includes an uncrosslinked polymer.

Embodiment 92 is a non-transitory machine readable medium having data representing a three-dimensional model of an article, when accessed by one or more processors interfacing with a 3D printer, causes the 3D printer to create an article. The article includes an integral blend of 8 to 50 wt. %, inclusive, of a thermoset polymer and 30 to 90 wt. %, inclusive, of a second polymer different from the thermoset polymer. The weight percent is based on the total weight of the article.

Embodiment 93 is a method including retrieving, from a non-transitory machine readable medium, data representing a 3D model of an article. The article includes: an integral blend of 8 to 50 wt. %, inclusive, of a thermoset polymer and 30 to 90 wt. %, inclusive, of a second polymer different from the thermoset polymer. The weight percent is based on the total weight of the article. The method further includes executing, by one or more processors, a 3D printing application interfacing with a manufacturing device using the data; and generating, by the manufacturing device, a physical object of the article.

Embodiment 94 is an article generated using the method of embodiment 93.

Embodiment 95 is the article of embodiment 94, wherein the article includes an orthodontic article.

Embodiment 96 is a method including: receiving, by a manufacturing device having one or more processors, a digital object including data specifying a plurality of layers of an article. The article includes an integral blend of 8 to 50 wt. %, inclusive, of a thermoset polymer and 30 to 90 wt. %, inclusive, of a second polymer different from the thermoset polymer. The weight percent is based on the total weight of the article. The method further includes generating, with the manufacturing device by an additive manufacturing process, the article based on the digital object.

Embodiment 97 is the method of embodiment 96, wherein the manufacturing device selectively cures a printable composition to form a gelled article. The printable composition includes: (a) 1 to 50 wt. %, inclusive, of a polymer; (b) 5 to 50 wt. %, inclusive, of a polymerizable component; (c) 10 to 80 wt. %, inclusive, of a temporary solvent; (d) 0.1 to 5 wt. %, inclusive, of a photoinitiator; and (e) an optional inhibitor in an amount of 0.001 to 1 wt. %, inclusive, if present; based on the total weight of the printable composition.

Embodiment 98 is the method of embodiment 97, further including removing at least a portion of the temporary solvent from the gelled article.

Embodiment 99 is the method of embodiment 97 or embodiment 98, further including curing unpolymerized polymerizable component remaining in the gelled article.

Embodiment 100 is the method of any of embodiments 96 to 99, wherein the article includes an orthodontic article.

Embodiment 101 is a system including: a display that displays a 3D model of an article; and one or more processors that, in response to the 3D model selected by a user, cause a 3D printer to create a physical object of an article. The article includes: an integral blend of 8 to 50 wt. %, inclusive, of a thermoset polymer and 30 to 90 wt. %, inclusive, of a second polymer different from the thermoset polymer, wherein the weight percent is based on the total weight of the article.

EXAMPLES

Objects and advantages of this disclosure are further illustrated by the following examples, but the particular materials and amounts thereof recited in these examples, as well as other conditions and details, should not be construed to unduly limit this disclosure.

Test Methods

Viscosity Test Method

The viscosity of the compositions was and can be tested according to ASTM D4287 using a CAP2000+ Viscometer, made by Brookfield AMETEK, Inc., Middleboro, Mass., USA.

Tensile Strength and Elongation Test Method

The mechanical properties of the objects were and can be tested by printing a test specimen conforming to the tensile bar shape described in ASTM D638-10, Type V. The width W of the narrow section is nominally 3.18 mm, the length L of the narrow section is 9.53 mm. The thickness of the specimen is 1 mm. The length overall LO of the specimen was reduced from the 63.5 mm to 48 mm by shortening each grip area by 7.75 mm. This is done to accommodate the tensile bar in the available print area in the Asiga PicoPlus39 printer. The specimens are tested in a tensile tester model Insight 5SL, made by MTS Systems Corp., Eden Prairie, Minn., using a 5 kN load cell at a speed of 5.1 mm/min.

Testing of Exemplary Compositions

The materials used in the following examples are summarized in Table 1.

TABLE 1

Summary of materials.

| Material | Description | Source |
| --- | --- | --- |
| Isopropyl Alcohol | 2-propanol (isopropyl alcohol) | VWR International LLC, Radnor, PA |
| EQ-C25 | Cocoalkylmethyl[polyxyethylene(15)] ammonium chloride, 95% minimum active surfactant solution, available under the trade designation ETHOQUAD C/25 | Akzo Nobel N.V., Amsterdam, Netherlands |
| DMAEA-MCl | Dimethylaminoethyl acrylate methyl chloride quaternary, 80% in water, available under the trade designation AGEFLEX FA1Q80MC. | BASF, Ludwigshafen, Germany |
| IOA | Isooctyl acrylate | 3M Company, St. Paul, MN |
| VAc | Vinyl acetate | Alfa Aesar, Ward Hill, MA |
| IBoA | Isobornyl Acrylate | Sartomer, Exton, PA |
| MAA | Methacrylic acid | Alfa Aesar, Ward Hill, MA |
| V-50 | 2,2'-Azobis (2-methylpropionamidine) dihydrochloride | Wako Chemicals Richmond, VA |
| SR415 | Ethoxylated (20) trimethylolproprane triacrylate | Sartomer, Exton, PA |
| SR9036A | Ethoxylated (30) Bisphenol A dimethacrylate | Sartomer, Exton, PA |
| IRGACURE 819DW | Phosphine oxide, phenylbis(2,4,6-trimethylbenzoyl) | BASF, Ludwigshafen, Germany |
| BHT | 2,6-Di-tert-butyl-4-methyl-phenol | Fluka Analytical, St. Louis, Mo |
| U6800 | Aliphatic polycarbonate/polyurethane dispersion, 32-34% solids | Alberdingk Boley Inc, Greensboro, NC |
| U3700 | Aqueous, anionic dispersion of an aliphatic polycarbonate polyurethane, 35-37% | Alberdingk Boley Inc, Greensboro, NC |
| LUX 481 | UV-curable polyurethane/acrylic copolymer dispersion, 39-41% solids | Alberdingk Boley Inc, Greensboro, NC |
| LUX 484 | UV-curable polyurethane dispersion, 36-38% solids | Alberdingk Boley Inc, Greensboro, NC |
| TA | Terephthalic Acid (0.753 # mols) | CEPSA Quimica of Montreal, Quebec |
| SSIPA | Sodiumsulfoisophthalic acid (0.087 # mols) | FutureFuel of Batesville, AR |
| IPA | Isophthalic Acid (0.745 # mols) | Eastman Chemical of Kingsport, TN |
| NPG | Neopentyl glycol (1.188 # mols) | Eastman Chemical of Kingsport, TN |
| EG | Ethylene Glycol (2.362 # mols) | ME Global of Midland, MI |
| AT | Antimony Triacetate | Arkema of Philadelphia, PA |
| SA | Sodium Acetate | Alfa Aesar of Ward Hill, MA |

Unless otherwise noted, all printed Examples were printed on an Asiga PicoPlus39, a vat polymerization 3D printer available from Asiga USA, Anaheim Hills, Calif.

Example 1. Zwitterionic Emulsion Polymer Synthesis

A clean one liter glass reactor was used, equipped with stirrer, reflux condenser, heat lamps, thermometer, temperature controller, and nitrogen purge. To the reactor was added DMAEA-MC1 (10 parts, 80% in water), IOA (85 parts), MAA (2 parts), and VA (5 parts), followed by EQ-C25 (1 part) dissolved in 100 parts of DI water. The mixture was stirred at 175 rpm and then purged with nitrogen for 30 minutes at 2 liters/minute of nitrogen.

Next, the reactor was set to be heated to 50° C. and, when the temperature was at 35° C., 0.375 parts of V-50 initiator was added. After 4 hours of heating at 50° C., a second charge of V-50 (0.1 parts) was added, the temperature increased to 65° C., then held at 65° C. for two hours. Next, the reaction mixture was allowed to cool to room temperature. The pH of the reaction mixture was then adjusted to 5.2 by adding aqueous sodium hydroxide solution, followed by filtering the reaction mixture through cheese cloth. A white milky emulsion was obtained without any coagulum. The conversion was quantitative as determined by % solids analysis.

By following the above process (except for pH adjustment) the rest of the polymers in Table 2 below were synthesized.

TABLE 2

Formulations of zwitterionic emulsion polymers

| ID | DMAEA-MCl | IOA | IBoA | VAc | MAA | EQ-C25 | V-50 | H2O | pH | Solids (%) |
|---|---|---|---|---|---|---|---|---|---|---|
| 1 | 8(10) | 85 | 0 | 5 | 2 | 1 | 0.375 | 100 | 5.2 | 48 |
| 2 | 8(10) | 65 | 20 | 5 | 2 | 1 | 0.375 | 100 | 2.5 | 49.70 |
| 3 | 8(10) | 55 | 30 | 5 | 2 | 1 | 0.375 | 100 | 2.5 | 49.50 |
| 4 | 8(10) | 45 | 40 | 5 | 2 | 1 | 0.375 | 100 | 2.5 | 49.60 |
| 5 | 8(10) | 35 | 50 | 5 | 2 | 1 | 0.375 | 100 | 2.5 | 50.37 |
| 6 | 8(10) | 25 | 60 | 5 | 2 | 1 | 0.375 | 100 | 2.5 | 49.80 |

Examples 2-7. Physical Properties of Polymers from Zwitterionic Emulsions

The Example 2 (E2) formulation shown in Table 3 below was mixed in a glass jar. The E2 mixture was placed on a rolling mixer to make a homogenous mixture. The mixture was degassed in a vacuum chamber for 30 minutes. The mixture was then poured in a silicone dogbone mold (Type IV mold, ASTM D638). The filled mold was placed between two glass plates and cured in a broad spectrum UV chamber (Dymax Light Curing Systems Model 2000 Flood) for 5 minutes. The sample was demolded and cured for another 5 minutes in the chamber. The dogbones (containing water) were then placed in a vacuum oven at 50° C. overnight to dry overnight. The final dogbone samples shrank 27.6% in volume. These dogbones were tested on an Insight MTS with 5 kN load cell at the rate of 5 mm/minute. Five replicate samples were tested. The tensile strength and elongation at break of the samples were determined and shown in Table 4 below.

Subsequent examples, E3-E7, were made similarly (the formulations are summarized in Table 3 below) and tested. The test results of the cast samples are summarized in Table 4 below.

TABLE 3

Photocurable Formulations with Emulsions

| Sample ID | Emulsion ID | Parts per hundred parts of resin (phr), of emulsion | Acrylate | phr of acrylate | IRGACURE 819DW | BHT |
|---|---|---|---|---|---|---|
| E3 | 4 | 85 | SR415 | 15 | 0.15 | 0.015 |
| E4 | 4 | 75 | SR415 | 25 | 0.25 | 0.025 |
| E7 | 5 | 85 | SR415 | 15 | 0.15 | 0.015 |
| E8 | 5 | 95 | SR9036A | 5 | 0.05 | 0.005 |
| E9 | 1 | 90 | SR415 | 10 | 0.1 | 0.01 |

TABLE 4

Mechanical Properties of Cast Emulsions

| Sample ID | Tensile Strength (Mpa) | Std Dev (Mpa) | Std Dev (Mpa) | Elongation at Break (%) | Std Dev (%) |
|---|---|---|---|---|---|
| E3 | 1.6 | 0.1 | 0.026 | 471.1 | 41.4 |
| E7 | 2.4 | 0.1 | 0.891 | 388 | 55.5 |
| E8 | 3.4 | 0.7 | 0.295 | 926.5 | 48.5 |
| E9 | 0.5 | 0.1 | 0.026 | 235.3 | 20.4 |

Example 8. Water Soluble Sulfopolyester

To a clean, dry oil jacketed 100 gallon stainless steel reactor, the following materials were added:
125.1 lbs (56.7 kg) of TA
23.4 lbs (10.6 kg) of SSIPA
123.7 lbs (56.1 kg) of IPA
123.7 lbs (56.1 kg) of NPG
146.8 lbs (66.6) of EG 126.6 g of AT
318.5 g of SA The kettle was placed under 30 psig of nitrogen pressure.

The contents of the vessel were heated and a typical PET transesterification took place. The batch was heated to ~485° F. (~252° C.). Once esterification was determined complete, pressure in the kettle was slowly vented.

A typical polyester polymerization commenced. Vacuum was slowly pulled on the kettle and heat was applied. Excess glycol was removed. Eventually, the kettle reached a temperature of 525° F. and a vacuum measuring as low as 1.5 mmHg. Once target IV of ~0.50 dL/g was achieved, the batch was pressurized (under nitrogen) and drained into trays. These trays of resin were ground up and utilized for WB-50 solution making. The resultant polymer was composed of ~5.5 mol % SSIPA, 47.5 mol % TA and 47 mol % IPA (on an acids basis); 75% mol % NPG and 25 mol % EG on a diols basis.

The solid form of WB-50 was combined with an 80/20 mixture of DI water and isopropanol. By weight, the initial mixture was composed of ~35% WB-50, ~48% water, and ~17% isopropanol. The mixture was stirred and heated to 75° C. on a set of heated rollers for 24 hours (or until a consistent mixture with no visible solids were formed). The solution was placed on a roto-vaporator at 75° C. and 400 mbar for 1 hour to remove the isopropanol. Using a moisture analyzer for 2 hours at 165° C., a small sample of the resulting mixture was measured to be ~41% solids. The 41% solids solution was combined with the water soluble acrylate, Sartomer SR415, and a water soluble initiator IRGACURE 819Dw at various concentrations, as shown in Table 5 below.

The dogbones (containing water) were then placed in a vacuum oven at 50° C. overnight to dry overnight. The final dogbone samples shrank based on the water content of the original mixture. The dried dogbones were placed in an oven at 75° C. for 48 hours to create an interpenetrating network. These dogbones were tested on an MTS Insight at the rate of 10.1 mm/minute. Five replicate examples were tested. The tensile strength and elongation at break of the samples were determined and shown in Table 6 below. Only samples with no significant defects from the molding and drying processes were tested.

TABLE 6

Material properties of cast polyester solutions

| Sample ID | % Polyester | Tensile Strength (MPa) | Std Dev (MPa) | Std Dev (Mpa) | Elongation at Break (%) | Std Dev (%) |
|---|---|---|---|---|---|---|
| WB-50 90/10 | 78.68 | 16.93 | 1.626 | 39.292 | 164.9 | 71.8 |
| WB-50 85/15 | 70.41 | 11.92 | 1.372 | 12.631 | 89.3 | 30.6 |
| WB-50 80/20 | 62.12 | 11.85 | 1.002 | 7.961 | 105.5 | 20.9 |

Example 10. Photocurable Formulations Using Polyurethane Dispersions

TABLE 7

Photocurable formulations with polyurethane dispersions

| Sample ID | PU Emulsion used | Parts per hundred parts of resin (phr), of emulsion | Acrylate | phr of acrylate | IRGACURE 819DW | BHT |
|---|---|---|---|---|---|---|
| U1 | U6800 | 80 | SR415 | 20 | 0.5 | 0.05 |
| U2 | U3700 | 70 | SR415 | 30 | 0.5 | 0.05 |
| U3 | LUX 481 | 85 | SR415 | 15 | 0.5 | 0.05 |
| U4 | LUX 484 | 85 | SR415 | 15 | 0.5 | 0.05 |

TABLE 5

Photocurable formulations with sulfopolyester

| Sample ID | 41% WB-50/H20 (g) | SR415 (g) | IRGACURE 819Dw (g) |
|---|---|---|---|
| WB-50 90/10 | 21.49 | 2.39 | 0.3161 |
| WB-50 85/15 | 27.43 | 4.85 | 0.363 |
| WB-50 80/20 | 16.66 | 4.16 | 0.211 |

Example 9

The formulations in Table 5 were each mixed separately in amber bottles overnight on a rolling mixer. The mixtures were each degassed in a vacuum chamber for 30 minutes. Each mixture was then poured in a silicone dogbone mold (Type IV mold, ASTM D638). The filled molds were placed between two glass plates and cured in a broad spectrum UV chamber for 5 minutes. The samples were demolded and post-cured for another 5 minutes in the UV chamber.

The formulations in Table 7 were each mixed separately in amber bottles overnight on a rolling mixer. The mixtures were each degassed in a vacuum chamber for 30 minutes. Each mixture was then poured in a silicone dogbone mold (Type IV mold, ASTM D638). The filled molds were placed between two glass plates and cured in a broad spectrum UV chamber for 5 minutes. The samples were demolded and post-cured for another 5 minutes in the UV chamber.

The dogbones (containing water) were then placed in a vacuum oven at 50° C. overnight to dry overnight. These dogbones were tested on an MTS Insight at the rate of 10.1 mm/minute. Only samples with no significant defects from the molding and drying processes were tested. Five replicate examples were tested. The tensile strength and elongation at break of the samples were determined and shown in Table 8 below.

TABLE 8

| | Mechanical Properties of Cast PU dispersions | | | | |
|---|---|---|---|---|---|
| Sample ID | Tensile Strength (Mpa) | Std Dev (Mpa) | Std Dev (Mpa) | Elongation at Break (%) | Std Dev (%) |
| U1 | 1.7 | 0.3 | 0.215 | 69.4 | 19.9 |
| U2 | 1.5 | 0.4 | 0.157 | 93.5 | 29.5 |
| U3 | 4.8 | 1.3 | 6.69 | 5.5 | 2.4 |
| U4 | 9.4 | 2 | 9.64 | 7.3 | 2.2 |

Example 11: Sulfopolyester-Acrylate Article Made Using Vat Polymerization

A 3D printed article was created using inverse vat polymerization using the aqueous solution of WB-50 as described in Example 9. In a clean amber bottle was mixed WB-50 (85 parts, 42% in water), SR415 (15 parts), Irgacure819Dw (1 part), and BHT (0.1 part). The mixture was placed on rollers for 24 hours to allow the components to mix into a printable resin.

An article was produced by stereolithography (vat polymerization) using a PICO 2 "3D printer" (energy source: 385 nm LED) from ASIGA Anaheim Hills, Calif., USA. The default settings were used except for the following settings: Slice thickness=50 µm, Burn-In Layers=1, Separation Velocity=5 mm/s, Slides per Layer=1, Burn-In Exposure Time=20.0 s, Normal Exposure Time=4.000 s. During printing, the resin was mixed every 15 minutes using a pipette to prevent the resin components from settling out in the vat.

Figure 5:
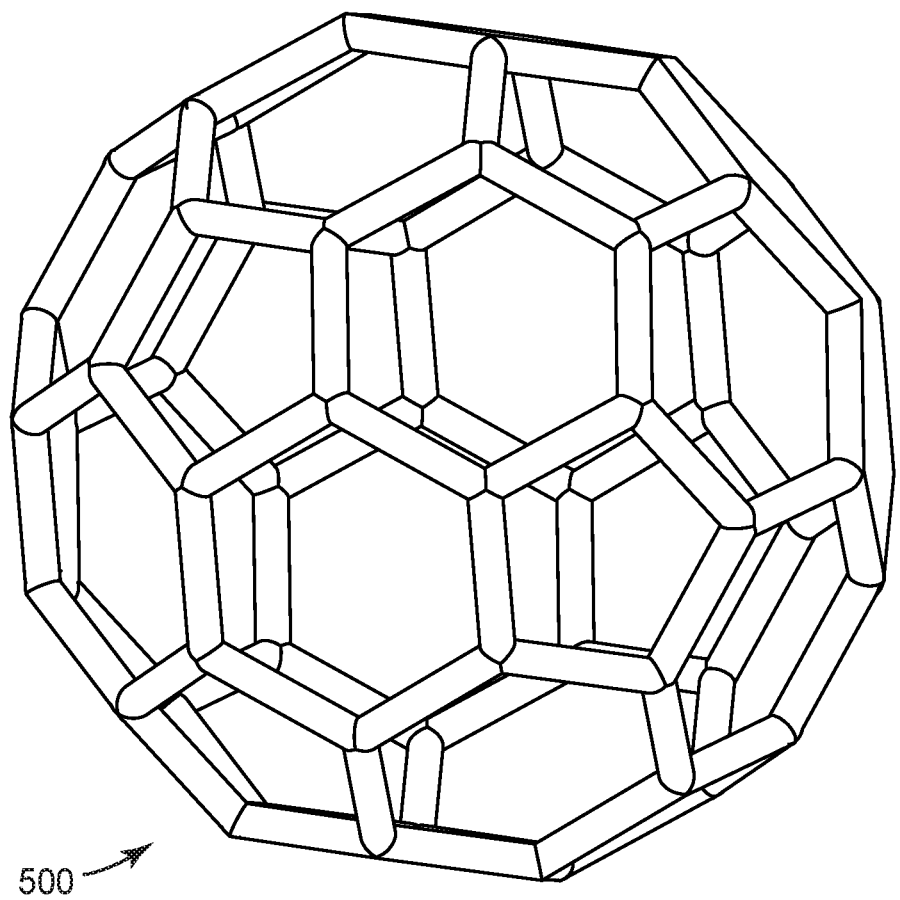
FIG. 5 is a schematic perspective view of a buckyball shape, preparable according to Example 11.

Using this method, the geometry of a buckyball measuring 25 mm in diameter was printed in the WB-50 resin. FIG. 5 provides a schematic perspective view of the shape of the buckyball 500. The gelled part was successfully removed from the build plate, rinsed with water and post cured in an ASIGA UV chamber for 15 minutes. The fully cured gel part was then dried in a vacuum oven at 50° C. for 24 hours. The fully dried part shrank to ~20 mm in diameter. The dried structure was placed in an oven at 75° C. for 72 hours to create an interpenetrating network within the polyester.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. A printable composition comprising:
   (a) 15 to 50 wt. %, inclusive, of a polymer selected from the group consisting of polyolefin, sulfopolyester, and polyethylene terephthalate;
   (b) 10 to 25 wt. %, inclusive, of a polymerizable component;
   (c) 10 to 80 wt. %, inclusive, of a temporary solvent, wherein the temporary solvent comprises water;
   (d) 0.1 to 5 wt. %, inclusive, of a photoinitiator; and
   (e) an optional inhibitor in an amount of 0.001 to 1 wt. %, inclusive, if present; based on the total weight of the printable composition.

2. The printable composition of claim 1, wherein the polymer comprises a weight average molecular weight of 20,000 grams per mole or greater.

3. The printable composition of claim 1, wherein the polymer is selected from the group consisting of polyethylene (PE), polypropylene, sulfopolyester, polyethylene terephthalate (PET), and combinations thereof.

4. The printable composition of claim 1, wherein the polymerizable component comprises urethane groups, epoxy groups, or both.

5. The printable composition of claim 1, wherein the printable composition has a viscosity of 15,000 cP or less at 25° C. using a #1 spindle.

6. The printable composition of claim 1, wherein the polymerizable component comprises an acrylate and/or a methacrylate.

7. The printable composition of claim 1, wherein the polymerizable component comprises a poly(meth)acrylate.

* * * * *

UNITED STATES PATENT AND TRADEMARK OFFICE
CERTIFICATE OF CORRECTION

PATENT NO. : 11,602,412 B2
APPLICATION NO. : 16/463560
DATED : March 14, 2023
INVENTOR(S) : Zeba Parkar et al.

Page 1 of 1

It is certified that error appears in the above-identified patent and that said Letters Patent is hereby corrected as shown below:

In the Claims

Column 40
Line 15, In Claim 1, delete "component;" and insert -- component, wherein the polymerizable component interpenetrates the polymer; --, therefor.

Signed and Sealed this
Tenth Day of October, 2023

Katherine Kelly Vidal
*Director of the United States Patent and Trademark Office*